US009328385B2

(12) United States Patent
Di Pasquale et al.

(10) Patent No.: US 9,328,385 B2
(45) Date of Patent: *May 3, 2016

(54) METHOD FOR QUANTIFYING HUMAN DNA USING AN INTERNAL CONTROL

(75) Inventors: Francesca Di Pasquale, Dusseldorf (DE); Holger Engel, Hilden (DE); Sascha Strauss, Solingen (DE); Nicola Jo Thelwell, Derbyshire (GB)

(73) Assignees: Qiagen GmbH, Hilden (DE); Qiagen Manchester Limited, Manchester (GB)

( * ) Notice: Subject to any disclaimer, the term of this patent is extended or adjusted under 35 U.S.C. 154(b) by 158 days.

This patent is subject to a terminal disclaimer.

(21) Appl. No.: 14/000,092

(22) PCT Filed: Feb. 20, 2012

(86) PCT No.: PCT/EP2012/000833
§ 371 (c)(1),
(2), (4) Date: Jan. 28, 2014

(87) PCT Pub. No.: WO2012/113577
PCT Pub. Date: Aug. 30, 2012

(65) Prior Publication Data
US 2014/0147843 A1 May 29, 2014

Related U.S. Application Data

(60) Provisional application No. 61/588,975, filed on Jan. 20, 2012.

(30) Foreign Application Priority Data

Feb. 21, 2011 (EP) ..................................... 11155178

(51) Int. Cl.
*C12P 19/34* (2006.01)
*C12Q 1/68* (2006.01)

(52) U.S. Cl.
CPC ............ *C12Q 1/6879* (2013.01); *C12Q 1/6851* (2013.01); *C12Q 1/6888* (2013.01); *C12Q 2600/16* (2013.01); *C12Q 2600/166* (2013.01)

(58) Field of Classification Search
CPC ........... C12Q 2545/114; C12Q 1/6846; C12Q 1/686; C12Q 1/6865; C12Q 2525/151; C12Q 2537/157; C12Q 2561/113; C12Q 1/6851; C12Q 1/6853
USPC ...................................................... 435/91.2
See application file for complete search history.

(56) References Cited

U.S. PATENT DOCUMENTS 7,374,927 B2   5/2008 Palma et al.
2007/0134655 A1   6/2007 Bentwich

FOREIGN PATENT DOCUMENTS

EP         0 714 987 A2      6/1996
WO      WO 03/075837         9/2003
WO      WO 2007/126377      11/2007
WO      WO 2012/038503       3/2012

OTHER PUBLICATIONS

Krenke et al., Developmental Validation of the Plexor HY system, PROMEGA Corporation, pp. 1-12, Dec. 2007.*
Niederstätter et al.; A modular real-time PCR concept for determining the quantity and quality of human nuclear and mitochondrial DNA; Forensic Science International: Genetics; vol. 1, No. 1, pp. 29-34; 2007.
Swango K. et al.: A quantitative PCR assay for the assessment of DNA degradation in forensic samples; Forensic Science International; vol. 158, No. 1, pp. 14-26; 2006.
P.H. Sudmant et al.: Diversity of Human Copy Number Variation and multicopy genes; Science, vol. 330, No. 6004; pp. 641-646; 2010.
*Homo sapiens* cosmid clone XXcos-2185C13 from 7; complete sequence; EMBL; Feb. 27, 2002; XP002627315, nts 16636-18635.
Database Nucleotide NCBI; Aug. 17, 2000; *Homo sapiens* chromosome Y clone RP11-363H7; Working Draft Sequence; XP002677807; retrieved from http://www.ncbi/nlm.nih.gov/nuccore Database accession No. AC011304; Nucleotides 81696-81825.
Krenke B et al.: Developmental validation of a real-time PCR assay for the simultaneous quantification of total human and male DNA; Forensic Science International: Genetics; vol. 3, No. 1, pp. 14-21; Dec. 1, 2008.
Thelwell N. et al.: Mode of action and application of Scorpion primers to mutation detection; Nucleic Acids Research Special Publication; vol. 28, No. 19, pp. 3752-3761; Oct. 1, 2000.
Janye A. Bates et al.; Scorpion ARMS primers for SNP real-time PCR detection and quantification of Pyrenophora teres; Molecular Plant Pathology; vol. 2, No. 5; pp. 275-280; Sep. 1, 2001.
Pierce K. et al.: Real-time PCR using molecular beacons for accurate detection of the Y chromosome in single human blastomeres.; Molecular Human Reproduction; vol. 6, No. 12, pp. 1155-1164; Dec. 2000.
Deal et al.: Comprehensive human genome amplification using multiple displacement amplification; 2002; Proc. Natl. Acad. Sci; USA; 99(8): 5261-5266.
Vincent et al.: Helicase-dependent isothermal DNA amplification; 2004; EMBO rep. 5(8): 795-800.
An et al,: Characterization of a thermostable UvrD helicase and its participation in helicase dependent amplification; 2005; J. Biol. Chem.; 2005; vol. 280, No. 32; pp. 28952-28958.

(Continued)

*Primary Examiner* — Cynthia B Wilder
(74) *Attorney, Agent, or Firm* — Fanelli Haag PLLC

(57) ABSTRACT

The present invention relates to a method for quantifying and/or detecting one or more nucleic acids of a genome in a sample, wherein in an amplification reaction, (i) a first nucleic acid is amplified, the locus that is amplified is a multicopy locus (MCL) within the genome, wherein the locus shares at least 80% sequence identity to a sequence according to SEQ ID NO. 1 over a stretch of 80 base pairs, and wherein the multicopy locus has copies on at least two different chromosomes, (ii) a second nucleic acid that has been added as an internal control (IC) is also amplified, and (iii) the amount of amplification product from the amplification of the first nucleic acid is determined.

21 Claims, 26 Drawing Sheets

(56) References Cited

OTHER PUBLICATIONS

Walker et al.: Strand displacement amplification-an isothermal, In vitro DNA amplification technique; 1992; Nucleic Acids Res. 20(7): 1691-6.

Liu et al.: Rolling Circle DNA synthesis: Small Circular Oligonucleotides as Efficient Templates for DNA Polymerases; 1996, J. Am. Chem. Soc.; 118:1587-1594.

Wang et al.: DNA amplification method tolerant to sample degradation; 2004; Genome Research 14: 2357-2366.

Dafforn et al.: Linear mRNA amplification from as little as 5 ng total RNA for global gene expression analysis; 2004; Biotechniques 37(5): 854-7.

Vuorinen et al.: Direct Detection of *Mycobacterium tuberculosis* Complex in Respiratory Specimens by Gen-Probe Amplified *Mycobacterium tuberculosis* Direct Test and Roche Amplicor *Mycobacterium tuberculosis* Test; J. Clin. Microbiol. 33: 1856-1859; 1995.

Van Ness et al.: Isothermal reactions for the amplification of oligonucleotides; 2003; Prox. Natl. Acad. Sci: USA; 100(8): 4504-4509.

Notomi et al.: Loop-mediated isothermal amplification of DNA; 2000; Nucleic Acids Res. 28(12): e63.

Piepenburg et al.: DNA Detection Using Recombination Proteins; 2006; PloS Biol. 4(7): 1115-1120.

Karlin et al.: Applications and statistics for multiple high-scoring segments in molecular sequences; Proc. Natl. Acad. Sci. USA 1993; 90: 5873-5877.

Altschul et al.: Basic Local Alignment Search Tool; J. Mo. Biol. 1990; 215: 403-410.

\* cited by examiner

Figure 6:
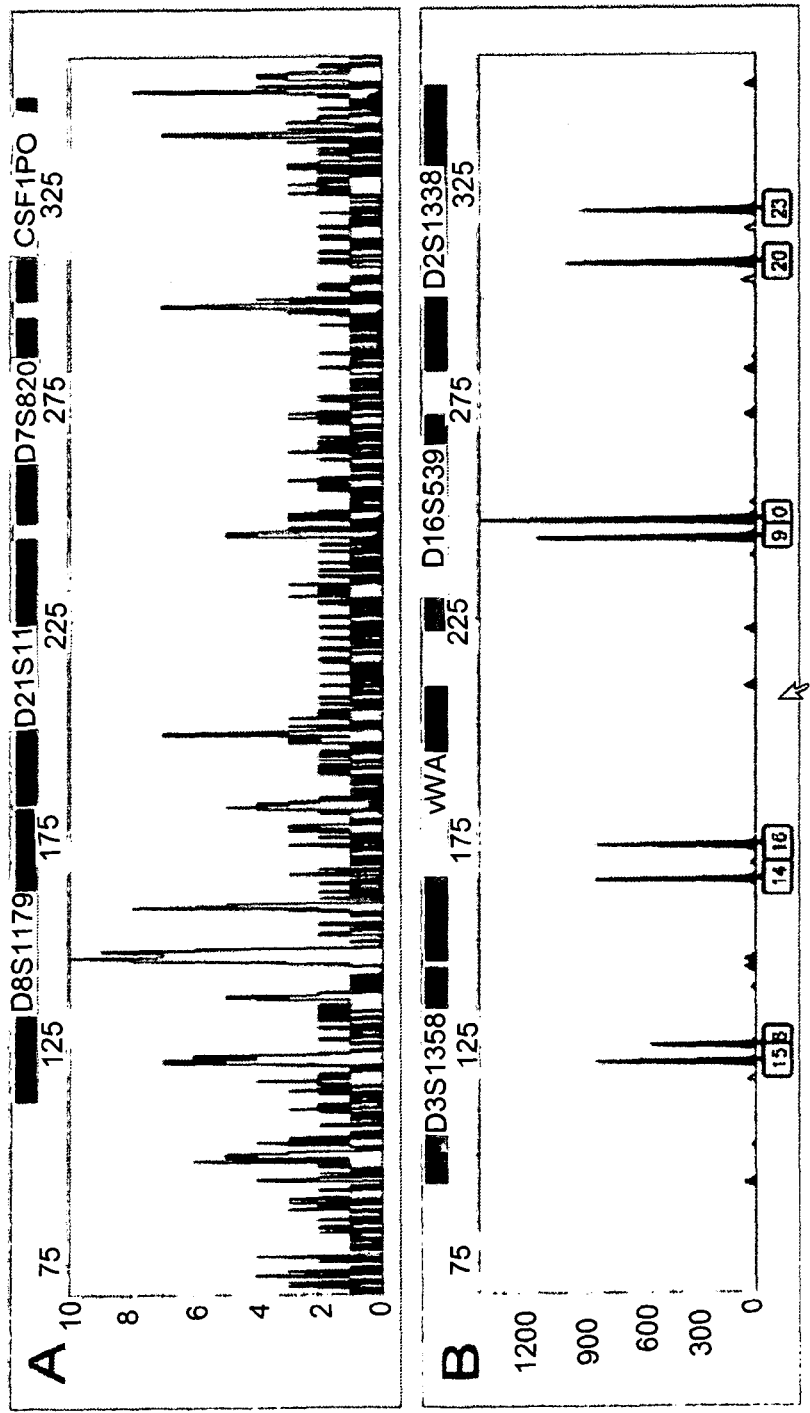
Figure 6:
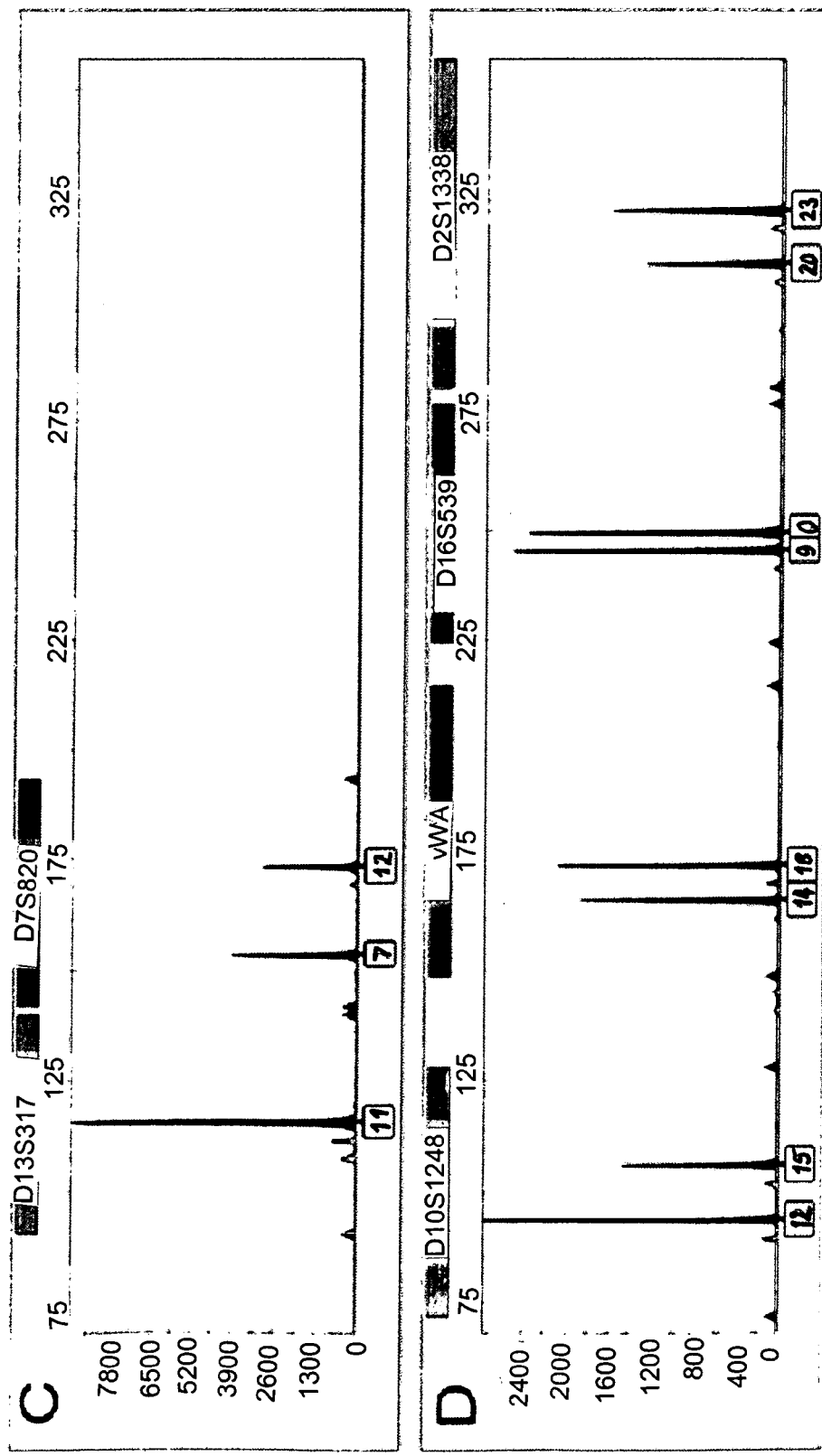
Figure 6:
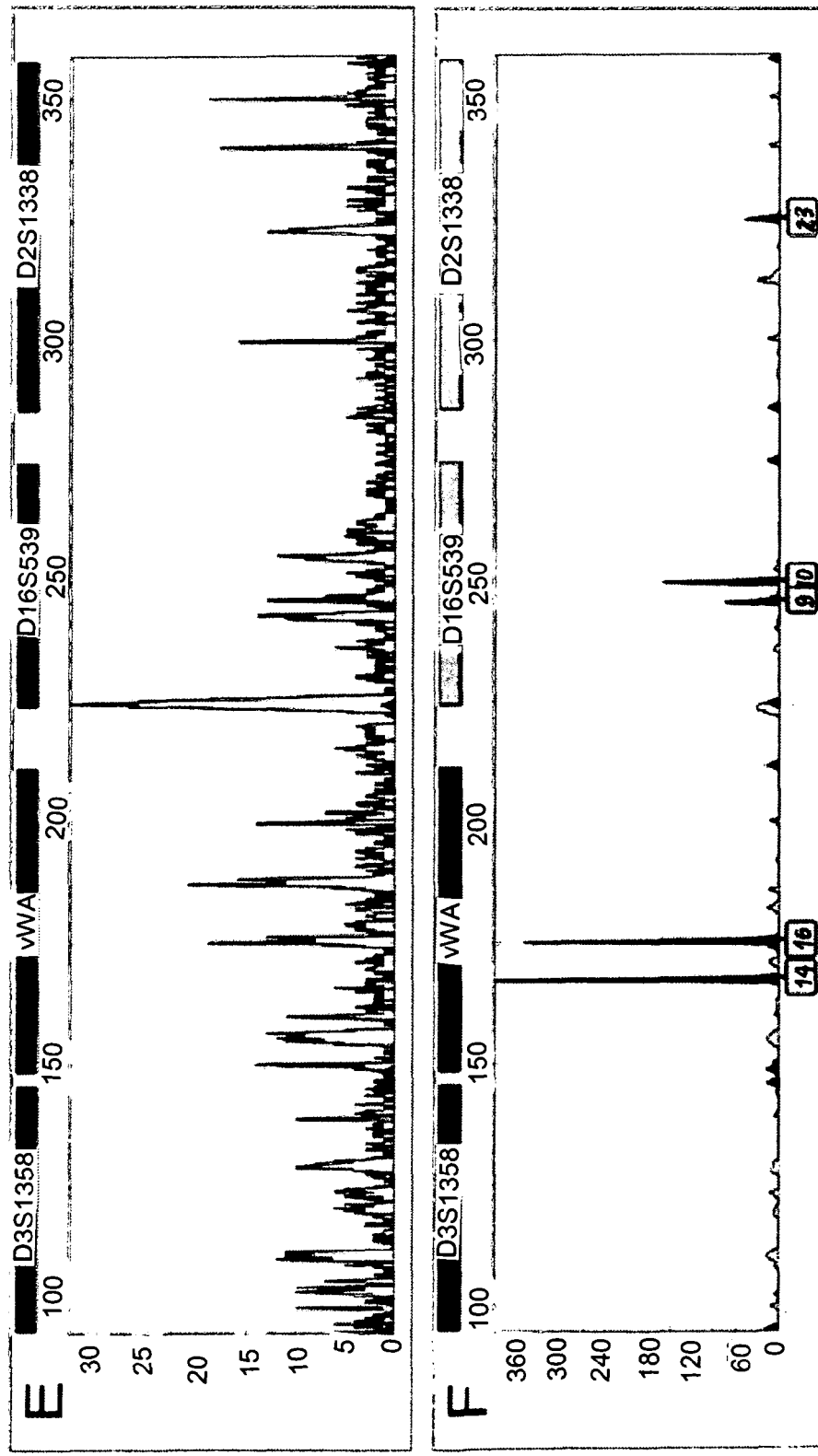
Figure 6:
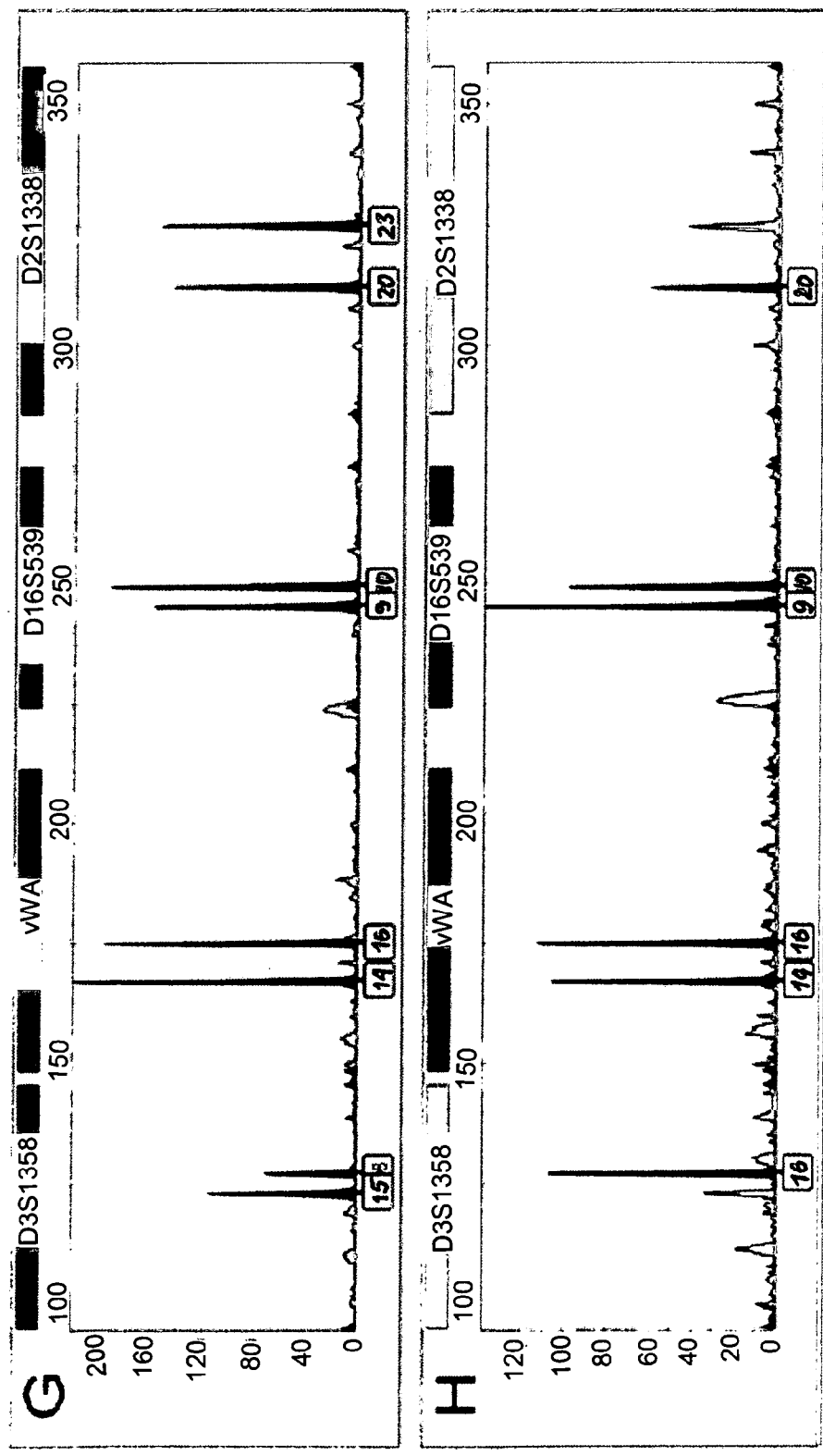
Figure 7:
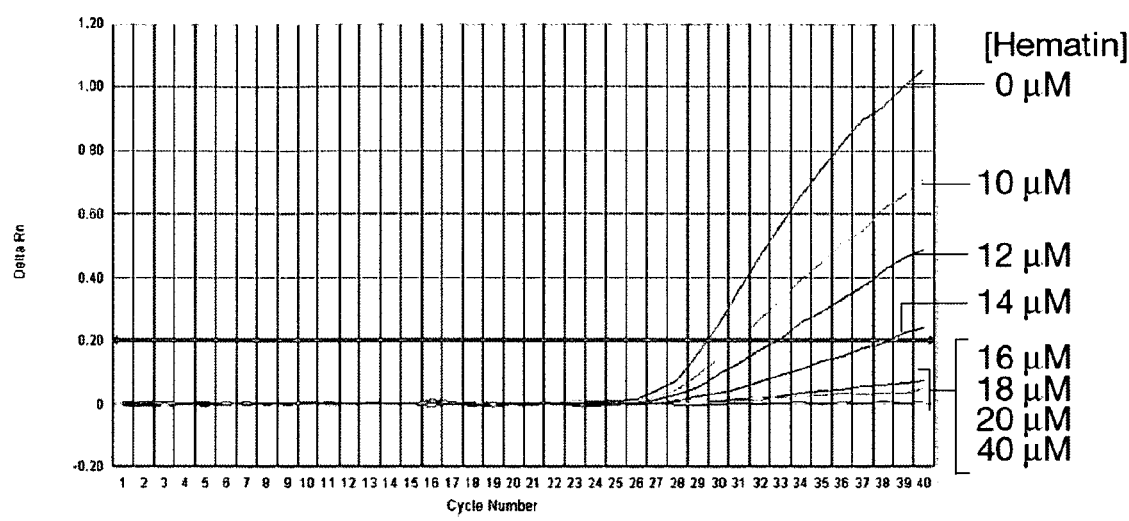

Fig. 7
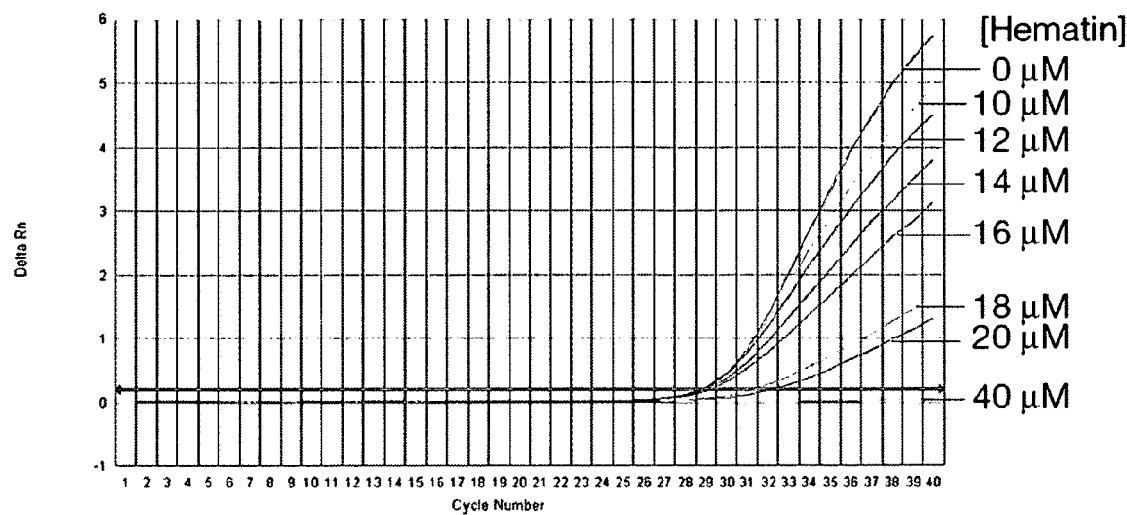
Inhibition studies: Quantifiler Human kit
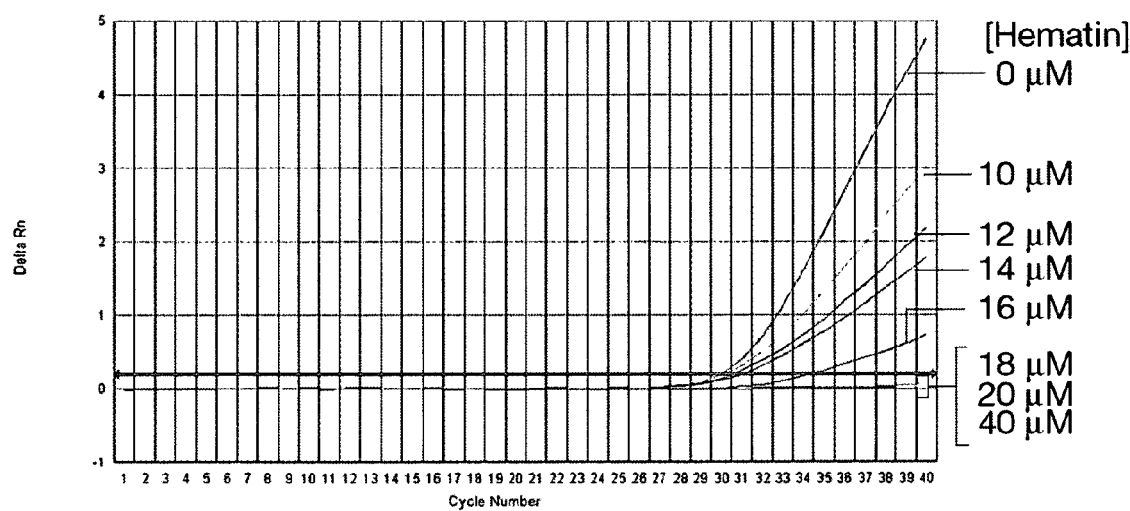
Inhibition studies: Quantifiler Y kit Inhibition studies: IPC detector Fig. 8
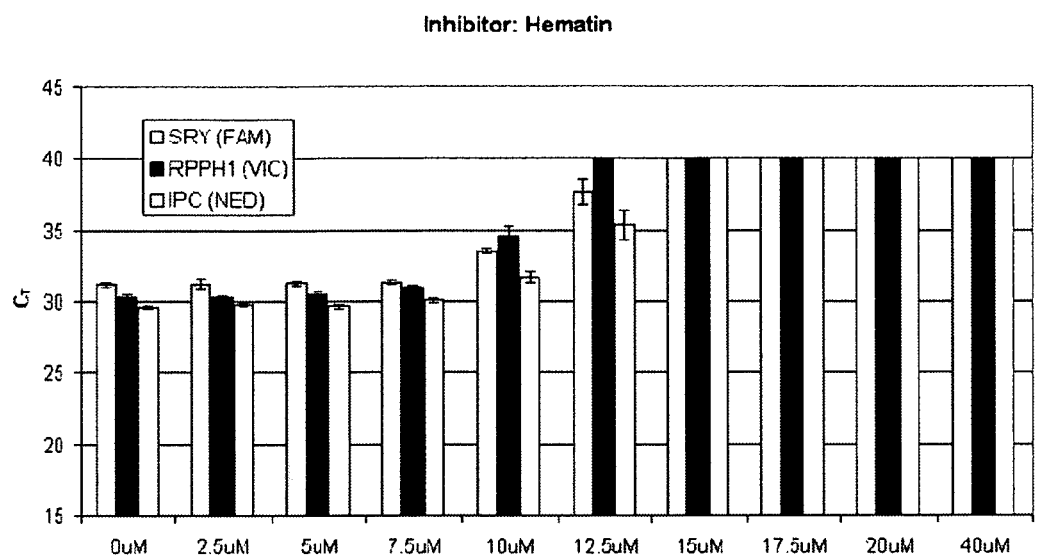
Figure 6-3  $C_T$ values for hematin-inhibited samples using the Quantifiler® Duo DNA Quantification Kit
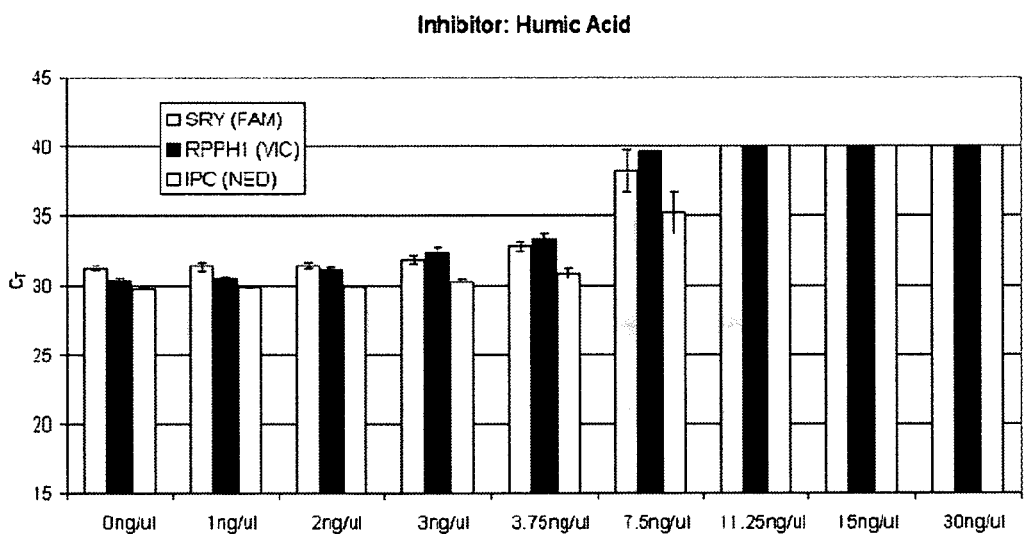
Figure 6-4  $C_T$ values for humic acid-inhibited samples using the Quantifiler® Duo DNA Quantification Kit

FIG. 11

| SEQ ID NO. 1 target sequence | 5'-TCAACAGGCCACCGTGAGGGAGGAGCTGGGCCGCACGCGGGCTGCTGG<br>GAGGCAGGCAGGGACTTGGCCCCGAGAGGCCGCCGTGGGGGCAAGAGC<br>TGGGCCTGGAGAGGCCCCTGGGAGGCAAGGGCGGGGCCTGCAGAGGCT<br>GTTCTCCAACCAGTGCTAGAACTGTACAGGCCACCAGGAGGCAGGAGG<br>TGGGCCCTCAGAGCTTGGCTGGAGAAAGTTCGGGGCCTACAAAGGCGG<br>TTGGGAGCTGGGCAGGAGTTGAGCCAAAAGAGCTTGCTTACTTGCTGG<br>GAGGCAGGGCCGGGAGAGCCCGACTTCAGGACAACTTGGGCCTGCGGC<br>AGTCGCCGGGAGGCCCAACCTTGGCGTGGAGGAGCCCACCGACCGGAG<br>ACCATTTGGGGCCTGGAGATGCCATCGGAGGGCAGGAGCTCATCCTGG<br>AGAGGCCACCGTGAGGCCTGACCTGGGCCTGGGGAGCTTGGCTTGAGG<br>AAGCTGTGGGCCGACCAAGGCCGCCAGGAGATGGGTAGGCACTGAGTC<br>CAAAGAGGTTGTTGAGAGGCAGGAATCGGGCCTGGAGACCCAACCAGG<br>AAGAAGAGCTGGGCCCGGAGAGAATGCACGGAGGGTGCAAGTGGGTCT<br>GGAGAGGCCGACTTGAGGAGGTTCTGGGCCCGGAGAGGCCGCCGGAAG<br>GGAAAAACTGGGCCTGGAAAGGCCGTTGTCAGGAATGAGCCCCATGGG<br>CCTGAAGAGGCCACTGGCAGGCGGGAGCTGGGCCTGCCGAAGCGGCCG<br>AGAGGCAGGAGCTTTGGACTCGGGAGGCCGCAGTGAAGCAACAGCTAG<br>CTGGGCGTGGAGAGTCCGCTGTGAGGCAGAGGCTGGGCCTGTGCAGGC<br>CTTCGGGAGGCAGGAGGCTGGGCCTTGTCGAGGCCTGCAGAGGCCACC<br>GAAAGTCAAAAGCGGGGCTTGGGAAGGCCGCCGGGAGGCATGAGCTGG<br>GCTGGGCCGAAAGAGGCCACTGGGAGGCAGGAGGAGCTGGGCCTGGAG<br>AGGCTGCCAAAAGGCAGGAGCTTCGCCTGAGGATGCCACAGTGAGACA<br>CCATCTGGGTCTGGAGGGTCCACTGTGAGGCAGAGGCTGACCTGTAGA<br>GTCCGACAGTAGACAGAAGTTGGGCAAAAGCCTGATTTGAGGAAGTTT<br>TGGGCTTCAAGAGTCAGCCACGAGGCAGGCACTAGGCCTGGAAATGGC<br>CTCACAGTCATGAGTTGGGCCTAAATGGGCCACTGTGAGGGAGGAGCT<br>GTGCCTGTTGAGGCTGCTGGCAGGCAGGCAGAAATTTGGCCTGGGGCA<br>GCTGCCATGAGGCAAGAGCTGGGCCTGGAAAAAGCCCCTGGGAGGCAA<br>GAGCAGGGCCTGCAGAGGCTGTTCTCAAGTCAAAGCTGGGCCTGTTGA<br>TGCCACCGGGAAGCAGAAGGTGGGCCTGGAGAGTTTGACTTGAGGAAG<br>TTTTGGGCCTACATTGGCCGCCATGAGCTGGACAGGAACTGGGCCAAA<br>AAAGGCTGTTGTGAGGCAGCAGTTGTGCCTGTAGACCCAGCCAAGAGG<br>AAGAGGTGGGTCTGGAGAAGCCCCCATGAGGCAGAGGTTGGGCCTGTA<br>GACGCTGACAGGAGGCAGGAGCTGGGCCTGGACAGGTCAACTTGAGGA<br>GATTTTGGGCCTTCATAGGCCACCAGGAGGCAGTAGTTGGGACTAGAG<br>AGTCTGACTTGAGTAAGTTTTGGGCCCGGAGATGACGTCCTGGGACAG<br>GAGTTGGGCGTGGAGAGGCCACCGTGAGGCATAAGCTGGATGTAGAGA<br>GGCCAGTGTGAGGCAAGACCTGGGCCTGTCTAGGCTGCTGGGAGACAG<br>GCAGGAATCTGGCCAGGGAAGGTTGCCATGAGACAAAAGTTGGGCCTG<br>GAAAGGCCCTTGTGAAGCATGAGCTTGGCCTAAAGAGGCCACTGGGTG<br>GCAGGAGCTGGGTGTGTAGAAGCTGCTGAAAGGTTGGGAGCTTGGCTT<br>GGGGGGTCCACAGTGAGGTAGATGCTGGGCGT-3' |
| SEQ ID NO. 2 hT-For1 (primer) | 5'-AGTGGGTCTGGAGAGGCCGACTTG-3' |
| SEQ ID NO. 3 hT-Rev1 | 5'-TCAGGCCCATGGGGCTCATTCCT-3' |

FIG. 11 continued

| | |
|---|---|
| (primer) | |
| SEQ ID NO. 4 hT-Pro1 (probe) | 5'-FAM-TTCTGGGCCCGGAGAGGCCGC-BHQ1-3' |
| SEQ ID NO. 5 hT-For2 (primer) | 5'-GCAGAAGGTGGGCCTGGAGAGTTTGAC-3' |
| SEQ ID NO. 6 hT-Rev2 (primer) | 5'-CCTTTTTTGGCCCAGTTCCTGTCCAGC-3' |
| SEQ ID NO. 7 hT-Pro2 (probe) | 5'-FAM-GGAAGTTTTGGGCCTACATTGGCCGCCATG-BHQ1-3' |
| SEQ ID NO. 8 hT-For3 (primer) | 5'-AAGGTGGGCCTGGAGAGTTT-3' |
| SEQ ID NO. 9 hT-Rev3 (primer) | 5'-CCTTTTTTGGCCCAGTTCCTGT-3' |
| SEQ ID NO. 10 hT-Pro3 (probe) | 5'-HEX-AAGTTTTGGGCCTACATTGGCCGC-BHQ1-3' |
| SEQ ID NO. 11 4NS1C Scorpion | 5'-Fam-CGAGCTCAGTTGTGCCTGTAGAGCTCG-dabcyl-C18-ACCTCTTCCTCTTGGCTGGG-3' |
| SEQ ID NO. 12 4NS1C primer | 5'-CCGGGAAGCAGAAGGTGG-3' |
| SEQ ID NO. 13 (AT-IC Rev) | 5'-GCTATCCAGTGTGCCTAGGCAA-3' |
| SEQ ID NO. 14 (AT-IC_Yak) | 5'-YAK-TGGCGTAGTCGTTCAACGCCA/Dabcyl/HEG/CCACGAGCGTACTTCGACTGAA-3' |

FIG. 16

| SEQ ID NO. 15 - Y chromosome reference sequence; | GGCTGAGTTCCTCCACCTGCCTGTCCAAGAAGGAGAAACAGGAC TGTGAAGGGACAATTTCATCTAGGTGGGCTGAGGTGGCCTGCTA GCTGGGGTGAAGCATGCGTTTCCCCTTCCCAGCTCTCCCACT |
|---|---|

| SEQ ID NO. 16 >chrY_235885 18_23588647_-/1-130 | ggctgagttcctccacctgcctgtccaagaaggagaaagaggatagtcaagggacagtttcatctaggtg ggctgaggtggcctgctagctggggtgaagcatgtgtttcccttcccagctctcccact |
|---|---|
| SEQ ID NO. 17 >chrY_236392 84_23639413_+/1-130 | ggctgagttcctccacctgcctgtccaagaaggagaaagaggatagtcaagggacagtttcatctaggtg ggctgaggtggcctgctagctggggtgaagcatgtgtttcccttcccagctctcccact |
| SEQ ID NO. 18 >chrY_244417 61_24441887_-/1-127 | agctgagttcctccacctgccaggccaaggagaagagtacagactcaaagggatgatttcatctagctgg gctgagggcctgctggctggggtgaagcatgtgtttccgcttcccagctctcctgct |
| SEQ ID NO. 19 >chrY_248172 87_24817413_+/1-127 | ggctgagttcctccacctgctacaccaagaagaagaggacagactcaaaggatccatttcatctagttggg ctgagggcctgctggctagggtgaagcatgcgtttcccttcccagctctcccact |
| SEQ ID NO. 20 >chrY_256710 61_25671187_-/1-127 | ggctgagttcctccacctgctacaccaagaagaagaggacagactcaaaggatccatttcatctagttggg ctgagggcctgctggctagggtgaagcatgcgtttcccttcccagctctcccact |
| SEQ ID NO. 21 >chrY_282917 23_28291849_+/1-127 | ggctgagttcctccacctgctacaccaagaagaagaggacagactcaaaggatccatttcatctagttggg ctgagggcctgctggctagggtgaagcatgcgtttcccttcccagctctcccact |
| SEQ ID NO. 22 >chrY_612351 2_6123641_+/1-130 | ggccgagttcctccacctgcctgtccaagaaggagaaacagggctgtgaaggggcaatttcatctaggtg ggctgaggtggcattctagccgggggtgaagcatgcgtttcccttcccagctttcccgct |
| SEQ ID NO. 23 >chrY_614214 0_6142268_+/1-129 | ggctgagttcttccacctgcctgtctgagaaggagaaagagatggtcaagggacaatttcatctaggtggg ctgaggtggcctgctagctggggtgaagcatgtgtttcccttcccagctctcccact |
| SEQ ID NO. 24 >chrY_812112 9_8121252_-/1-124 | ggccgagttcctccacctgccaggccaagaagaggacagactcaaagtgaccatttcatttagctgtgctg agggcctgctggctggagtgaagcatgcgtttcccttcccagctctccctct |
| SEQ ID NO. 25 >chrY_908638 2_9086511_+/1 | ggctgagttcctccacctgcctgtccaagaaggagaaagaggatggtcaagggacaatttcatctaggtc agctgaggggcctgctggctggggcgaagcatgcgatttcccttcccagctctccatt |

FIG. 16 continued

| | |
|---|---|
| -130 | |
| SEQ ID NO. 26 >chrY_9184321_9184450_+/1-130 | ggccgagttcctccacctgcctgtccaagaaggagaaacagggctgtgaaggggcaatttcatctaggtg ggctgaggtggcattctagccgggtgaagcatgcgtttccccttcccagctttcccgct |
| SEQ ID NO. 27 >chrY_9204614_9204743_+/1-130 | ggccgagttcctccacctgcctgtccaagaaggagaaacagggctgtgaaggggcaatttcatctaggtg ggctgaggtggcattctagccgggtgaagcatgcgtttccccttcccagctttcccgct |
| SEQ ID NO. 28 >chrY_9224932_9225061_+/1-130 | ggccgagttcctccacctgcctgtccaagaaggagaaacagggctgtgaaggggcaatttcatctaggtg ggctgaggtggcattctagccgggtgaagcatgcgtttccccttcccagctttcccgct |
| SEQ ID NO. 29 >chrY_9293487_9293616_+/1-130 | ggccgagttcctccacctgcctgtccaagaaggagaaacagggctgtgaaggggcaatttcatctaggtg ggctgaggtggcattctagccgggtgaagcatgcgtttccccttcccagctttcccgct |
| SEQ ID NO. 30 >chrY_9313796_9313925_+/1-130 | ggccgagttcctccacctgcctgtccaagaaggagaaacagggctgtgaaggggcaatttcatctaggtg ggctgaggtggcattctagccgggtgaagcatgcgtttccccttcccagctttcccgct |
| SEQ ID NO. 31 >chrY_9334098_9334227_+/1-130 | ggccgagttcctccacctgcctgtccaagaaggagaaacagggctgtgaaggggcaatttcatctaggtg ggctgaggtggcattctagccgggtgaagcatgcgtttccccttcccagctttcccgct |
| SEQ ID NO. 32 >chrY_9354410_9354539_+/1-130 | ggccgagttcctccacctgcctgtccaagaaggagaaacagggctgtgaaggggcaatttcatctaggtg ggctgaggtggcactctagccgggtgaagcatgcgtttccccttcccagctttcccgct |
| SEQ ID NO. 33 >chrY_9374716_9374845_+/1-130 | ggccgagttcctccacctgcctgtccaagaaggagaaacagggctgtgaaggggcaatttcatctaggtt ggctgaggtggcattctagccgggtgaagcatgcgtttccccttcccagctttcccact |
| SEQ ID NO. 34 >chrY_9738106_9738234_-/1-129 | ggctgagttcttccacctgcctgtctgagaaggagaaagagatggtcaagggacaatttcatctaggtggg ctgaggtggcctgctagctggggtgaagcatgtgtttccccttcccagctctcccact |
| SEQ ID NO. 35 >chrY_9875359_9875489_-/1-131 | ggctgagttccccactacctggccaagaagaagaaagaggacagactcaaaggagcatttcatgtagct gggctgaggtgacttgctagctggggtgaagcatgtgtttctccttcccagctctcccact |
| SEQ ID NO. 36 >chrY_9896242_9896371_-/1-130 | ggctgagttcctccacctgcctgtccaagaaggagaaagaggatggtcaagggacaatttcatctaggtg ggctgaggtggcctgctagctggggtgaagcatgcgtttcccctttccagctctcccact |

SEQUENCE LISTING

```
<160> NUMBER OF SEQ ID NOS: 38

<210> SEQ ID NO 1
<211> LENGTH: 2000
<212> TYPE: DNA
<213> ORGANISM: Homo sapiens

<400> SEQUENCE: 1
tcaacaggcc accgtgaggg aggagctggg ccgcacgcgg gctgctggga ggcaggcagg      60
gacttggccc cgagaggccg ccgtgggggc aagagctggg cctggagagg cccctgggag    120
gcaagggcgg ggcctgcaga ggctgttctc caaccagtgc tagaactgta caggccacca    180
ggaggcagga ggtgggccct cagagcttgg ctggagaaag ttcggggcct acaaaggcgg    240
ttgggagctg ggcaggagtt gagccaaaag agcttgctta cttgctggga ggcagggccg    300
ggagagcccg acttcaggac aacttgggcc tgcggcagtc gccgggaggc ccaaccttgg    360
cgtggaggag cccaccgacc ggagaccatt tggggcctgg agatgccatc ggagggcagg    420
agctcatcct ggagaggcca ccgtgaggcc tgacctgggc ctggggagct tggcttgagg    480
aagctgtggg ccgaccaagg ccgccaggag atgggtaggc actgagtcca aagaggttgt    540
tgagaggcag gaatcgggcc tggagaccca accaggaaga agagctgggc ccggagagaa    600
tgcacggagg gtgcaagtgg gtctgagag gccgacttga ggaggttctg ggcccggaga    660
ggccgccgga agggaaaaac tgggcctgga aaggccgttg tcaggaatga gccccatggg    720
```

```
cctgaagagg ccactggcag gcgggagctg ggcctgccga agcggccgag aggcaggagc    780
tttggactcg ggaggccgca gtgaagcaac agctagctgg gcgtggagag tccgctgtga    840
ggcagaggct gggcctgtgc aggccttcgg gaggcaggag gctgggcctt gtcgaggcct    900
gcagaggcca ccgaaagtca aaagcggggc ttgggaaggc cgccgggagg catgagctgg    960
gctgggccga agaggccac tgggaggcag gaggagctgg gcctggagag gctgccaaaa    1020
ggcaggagct cgcctgagg atgccacagt gagacaccat ctgggtctgg agggtccact    1080
gtgaggcaga ggctgacctg tagagtccga cagtagacag aagttgggca aaagcctgat    1140
ttgaggaagt tttgggcttc aagagtcagc cacgaggcag gcactaggcc tggaaatggc    1200
ctcacagtca tgagttgggc ctaaatgggc cactgtgagg gaggagctgt gcctgttgag    1260
gctgctggca ggcaggcaga aatttggcct ggggcagctg ccatgaggca agagctgggc    1320
ctggaaaaag cccctgggag gcaagagcag ggcctgcaga ggctgttctc aagtcaaagc    1380
tgggcctgtt gatgccaccg ggaagcagaa ggtgggcctg gagagtttga cttgaggaag    1440
ttttgggcct acattggccg ccatgagctg gacaggaact gggccaaaaa aggctgttgt    1500
gaggcagcag ttgtgcctgt agacccagcc aagaggaaga ggtgggtctg gagaagcccc    1560
catgaggcag aggttgggcc tgtagacgct gacaggagga ggagctggg cctggacagg    1620 tcaacttgag gagattttgg gccttcatag gccaccagga ggcagtagtt gggactagag    1680
agtctgactt gagtaagttt tgggcccgga gatgacgtcc tgggacagga gttgggcgtg    1740
gagaggccac cgtgaggcat aagctggatg tagagaggcc agtgtgaggc aagacctggg    1800
cctgtctagg ctgctgggag acaggcagga atctggccag ggaaggttgc catgagacaa    1860
aagttgggcc tggaaaggcc cttgtgaagc atgagcttgg cctaaagagg ccactgggtg    1920
gcaggagctg ggtgtgtaga agctgctgaa aggttgggag cttggcttgg ggggtccaca    1980
gtgaggtaga tgctgggcgt                                                2000

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agtgggtctg gagaggccga cttg                                            24

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcaggcccat ggggctcatt cct                                             23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 4
ttctgggccc ggagaggccg c                                        21

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcagaaggtg ggcctggaga gtttgac                                  27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6 cctttttttgg cccagttcct gtccagc                                 27

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ggaagttttg ggcctacatt ggccgccatg                               30

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaggtgggcc tggagagttt                                          20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 cctttttttgg cccagttcct gt                                      22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 10
aagttttggg cctacattgg ccgc                                          24

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgagctcagt tgtgcctgta gagctcgacc tcttcctctt ggctggg                 47

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccgggaagca gaaggtgg                                                 18

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctatccagt gtgcctaggc aa                                            22

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggcgtagtc gttcaacgcc accacgagcg tacttcgact gaa                     43

<210> SEQ ID NO 15
<211> LENGTH: 130
<212> TYPE: DNA
<213> ORGANISM: Homo sapiens

<400> SEQUENCE: 15
ggctgagttc ctccacctgc ctgtccaaga aggagaaaca ggactgtgaa gggacaattt   60
catctaggtg ggctgaggtg gcctgctagc tggggtgaag catgcgtttc cccttcccag  120
ctctcccact                                                         130

<210> SEQ ID NO 16
<211> LENGTH: 130
<212> TYPE: DNA
<213> ORGANISM: Homo sapiens

<400> SEQUENCE: 16
ggctgagttc ctccacctgc ctgtccaaga aggagaaaga ggatagtcaa gggacagttt    60
catctaggtg ggctgaggtg gcctgctagc tggggtgaag catgtgtttc cccttcccag   120
ctctcccact                                                         130

<210> SEQ ID NO 17
<211> LENGTH: 130
<212> TYPE: DNA
<213> ORGANISM: Homo sapiens

<400> SEQUENCE: 17
ggctgagttc ctccacctgc ctgtccaaga aggagaaaga ggatagtcaa gggacagttt    60
catctaggtg ggctgaggtg gcctgctagc tggggtgaag catgtgtttc cccttcccag   120
ctctcccact                                                         130

<210> SEQ ID NO 18
<211> LENGTH: 127
<212> TYPE: DNA
<213> ORGANISM: Homo sapiens

<400> SEQUENCE: 18
agctgagttc ctccacctgc caggccaagg agaagagtac agactcaaag ggatgatttc    60
atctagctgg gctgagggcc tgctggctgg ggtgaagcat gtgtttccgc ttcccagctc   120
tcctgct                                                            127

<210> SEQ ID NO 19
<211> LENGTH: 127
<212> TYPE: DNA
<213> ORGANISM: Homo sapiens

<400> SEQUENCE: 19
ggctgagttc ctccacctgc tacaccaaga agaagaggac agactcaaag gatccatttc    60
atctagttgg gctgagggcc tgctggctag ggtgaagcat gcgttttccc ttcccagctc   120
tcccact                                                            127

<210> SEQ ID NO 20
<211> LENGTH: 127
<212> TYPE: DNA
<213> ORGANISM: Homo sapiens

<400> SEQUENCE: 20
ggctgagttc ctccacctgc tacaccaaga agaagaggac agactcaaag gatccatttc    60
atctagttgg gctgagggcc tgctggctag ggtgaagcat gcgttttccc ttcccagctc   120
tcccact                                                            127

<210> SEQ ID NO 21
<211> LENGTH: 127
<212> TYPE: DNA
<213> ORGANISM: Homo sapiens

<400> SEQUENCE: 21
ggctgagttc ctccacctgc tacaccaaga agaagaggac agactcaaag gatccatttc    60
atctagttgg gctgagggcc tgctggctag ggtgaagcat gcgttttccc ttcccagctc   120
tcccact                                                            127

```
<210> SEQ ID NO 22
<211> LENGTH: 130
<212> TYPE: DNA
<213> ORGANISM: Homo sapiens

<400> SEQUENCE: 22
ggccgagttc ctccacctgc ctgtccaaga aggagaaaca gggctgtgaa ggggcaattt      60
catctaggtg ggctgaggtg gcattctagc cggggtgaag catgcgtttc cccttcccag     120 cttttcccgct                                                          130

<210> SEQ ID NO 23
<211> LENGTH: 129
<212> TYPE: DNA
<213> ORGANISM: Homo sapiens

<400> SEQUENCE: 23
ggctgagttc ttccacctgc ctgtctgaga aggagaaaga gatggtcaag ggacaatttc      60
atctaggtgg gctgaggtgg cctgctagct ggggtgaagc atgtgtttcc ccttcccagc     120
tctcccact                                                            129

<210> SEQ ID NO 24
<211> LENGTH: 124
<212> TYPE: DNA
<213> ORGANISM: Homo sapiens

<400> SEQUENCE: 24
ggccgagttc ctccacctgc caggccaaga agaggacaga ctcaaagtga ccatttcatt      60
tagctgtgct gagggcctgc tggctggagt gaagcatgcg tttccccttc ccagctctcc     120
ctct                                                                 124

<210> SEQ ID NO 25
<211> LENGTH: 130
<212> TYPE: DNA
<213> ORGANISM: Homo sapiens

<400> SEQUENCE: 25
ggctgagttc ctccacctgc ctgtccaaga aggagaaaga ggatggtcaa gggacaattt      60
catctaggtc agctgagggg gcctgctggc tgggcgaag catgcgattt cccttcccag     120
ctctcccatt                                                           130

<210> SEQ ID NO 26
<211> LENGTH: 130
<212> TYPE: DNA
<213> ORGANISM: Homo sapiens

<400> SEQUENCE: 26
ggccgagttc ctccacctgc ctgtccaaga aggagaaaca gggctgtgaa ggggcaattt      60
catctaggtg ggctgaggtg gcattctagc cggggtgaag catgcgtttc cccttcccag     120 cttttcccgct                                                          130

<210> SEQ ID NO 27
<211> LENGTH: 130
<212> TYPE: DNA
<213> ORGANISM: Homo sapiens
```

<400> SEQUENCE: 27
ggccgagttc ctccacctgc ctgtccaaga aggagaaaca gggctgtgaa ggggcaattt    60
catctaggtg ggctgaggtg gcattctagc cggggtgaag catgcgtttc cccttcccag   120
ctttcccgct                                                          130

<210> SEQ ID NO 28
<211> LENGTH: 130
<212> TYPE: DNA
<213> ORGANISM: Homo sapiens

<400> SEQUENCE: 28
ggccgagttc ctccacctgc ctgtccaaga aggagaaaca gggctgtgaa ggggcaattt    60
catctaggtg ggctgaggtg gcattctagc cggggtgaag catgcgtttc cccttcccag   120
ctttcccgct                                                          130

<210> SEQ ID NO 29
<211> LENGTH: 130
<212> TYPE: DNA
<213> ORGANISM: Homo sapiens

<400> SEQUENCE: 29
ggccgagttc ctccacctgc ctgtccaaga aggagaaaca gggctgtgaa ggggcaattt    60
catctaggtg ggctgaggtg gcattctagc cggggtgaag catgcgtttc cccttcccag   120
ctttcccgct                                                          130

<210> SEQ ID NO 30
<211> LENGTH: 130
<212> TYPE: DNA
<213> ORGANISM: Homo sapiens

<400> SEQUENCE: 30
ggccgagttc ctccacctgc ctgtccaaga aggagaaaca gggctgtgaa ggggcaattt    60
catctaggtg ggctgaggtg gcattctagc cggggtgaag catgcgtttc cccttcccag   120
ctttcccgct                                                          130

<210> SEQ ID NO 31
<211> LENGTH: 130
<212> TYPE: DNA
<213> ORGANISM: Homo sapiens

<400> SEQUENCE: 31
ggccgagttc ctccacctgc ctgtccaaga aggagaaaca gggctgtgaa ggggcaattt    60
catctaggtg ggctgaggtg gcattctagc cggggtgaag catgcgtttc cccttcccag   120
ctttcccgct                                                          130

<210> SEQ ID NO 32
<211> LENGTH: 130
<212> TYPE: DNA
<213> ORGANISM: Homo sapiens

<400> SEQUENCE: 32
ggccgagttc ctccacctgc ctgtccaaga aggagaaaca gggctgtgaa ggggcaattt    60
catctaggtg ggctgaggtg gcactctagc cggggtgaag catgcgtttc cccttcccag   120
ctttcccgct                                                          130

```
<210> SEQ ID NO 33
<211> LENGTH: 130
<212> TYPE: DNA
<213> ORGANISM: Homo sapiens

<400> SEQUENCE: 33
ggccgagttc ctccacctgc ctgtccaaga aggagaaaca gggctgtgaa ggggcaattt      60
catctaggtt ggctgaggtg gcattctagc cggggtgaag catgcgtttc cccttcccag     120
ctttcccact                                                            130

<210> SEQ ID NO 34
<211> LENGTH: 129
<212> TYPE: DNA
<213> ORGANISM: Homo sapiens

<400> SEQUENCE: 34
ggctgagttc ttccacctgc ctgtctgaga aggagaaaga gatggtcaag ggacaatttc      60
atctaggtgg gctgaggtgg cctgctagct ggggtgaagc atgtgtttcc ccttcccagc     120
tctcccact                                                             129

<210> SEQ ID NO 35
<211> LENGTH: 131
<212> TYPE: DNA
<213> ORGANISM: Homo sapiens

<400> SEQUENCE: 35
ggctgagttc ccccactacc tggccaagaa gaagaaagag gacagactca aaggagcatt      60
tcatgtagct gggctgaggt gacttgctag ctggggtgaa gcatgtgttt ctccttccca     120
gctctcccac t                                                          131

<210> SEQ ID NO 36
<211> LENGTH: 130
<212> TYPE: DNA
<213> ORGANISM: Homo sapiens

<400> SEQUENCE: 36
ggctgagttc ctccacctgc ctgtccaaga aggagaaaga ggatggtcaa gggacaattt      60
catctaggtg ggctgaggtg gcctgctagc tggggtgaag catgcgtttc ccctttccag     120
ctctcccact                                                            130

<210> SEQ ID NO 37
<211> LENGTH: 20
<212> TYPE: DNA
<213> ORGANISM: Homo sapiens

<400> SEQUENCE: 37
tggctgagtt cctccacctg                                                  20

<210> SEQ ID NO 38
<211> LENGTH: 43
<212> TYPE: DNA
<213> ORGANISM: Homo sapiens

<400> SEQUENCE: 38
cgaccgtgaa gcatgcgttt cggtcgagtg ggagagctgg gaa                        43
```

METHOD FOR QUANTIFYING HUMAN DNA USING AN INTERNAL CONTROL

This application is a National Stage of PCT/EP2012/000833, filed Feb. 20, 2012 which claims priority to European Application No. 11155178.4, filed Feb. 21, 2011 and U.S. Provisional Application No. 61/588,975, filed Jan. 20, 2012, the disclosures of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Sep. 10, 2013, is named 0051MA01US1SequenceListing.txt and is 12,983 bytes in size.

FIELD OF THE INVENTION

The present invention is in the field of molecular biology, diagnostics, more particularly in the field of analytical and forensic sciences. The invention is further in the field of nucleic acid amplification and quantification, more particularly in the field of DNA quantification.

Moreover, the early assessment of the presence of different contributors in a DNA stain is often a very important piece of information during an investigation. In this case, the STR analysis will result difficult because of the interference of the multiple contributors.

A particular case of a mixed sample is the sexual assault stain containing a mixture of female and male DNA. The accurate determination of the male: female DNA ratio helps in the selection of the optimal downstream STR analysis. In the case of a very low amount of available offender DNA a particular type of STR analysis can be carried out addressing genetic elements present exclusively on the Y-chromosome, thus excluding the interference of the female contribution.

The instant application contains a Sequence Listing which has been submitted in ASCII format via EFS-Web and is hereby incorporated by reference in its entirety. Said ASCII copy, created on Aug. 16, 2013, is named 0051_MA01US1_Sequence_Listing.txt and is 16685 bytes in size.

BACKGROUND

The determination of the quantity of DNA recovered from forensic samples as well as other samples is a critical step in the over all DNA typing process, but also in the detection of DNA in various other fields of science. A narrow range of input DNA from 0.5 to 2 ng is often needed to produce optimal results with for example multiplex DNA typing kits. Therefore, in order to ensure that a positive result is a positive result and/or a negative result is a negative result due to the absence of DNA, quantification of DNA is of absolute importance. Furthermore, the quality of standards for forensic DNA testing laboratories requires human-specific DNA quantification. This is due to isolation techniques that can recover human DNA as well as bacterial and other exogenous DNA. A number of procedures have been developed to permit quantification of human-specific DNA including start-blot techniques, liquid based hybridization assays and real-time PCR (polymerase chain reaction). Currently, real-time PCR is the dominant technique due to its wide dynamic range and ease of automation.

The modern STR-Kits have become much more sensitive and can obtain good results even using low amounts of DNA. Therefore, there is a desire for a method, kit and nucleic acid region that allows precise and accurate quantification of human DNA even in low concentrated samples. There are certain quantification and detection kits already available, however, these have serious drawbacks. One such kit is the Quantifiler Human Kit (Applied Biosystems) another kit is Quantifier Duo Kit (Applied Biosystems) another kit is the Plexor HY Real-Time PCR Quantification Kit (Promega). Both the Quantifiler Duo Kit and the Plexor HY Kit target an autosomal and a gonosomal (Y-chromosome) target on the genome. Drawbacks for the kits: According to LaSalle et al., (Forensic Science International: Genetics, "Analysis of Single and Multi-copy Methods for DNA Quantification by Real-Time Polymerase Chain Reaction") the Quantifier Kits are more accurate in the quantification but have a lower dynamic range as the Plexor HY. The Plexor HY offers a higher dynamic range due to the amplification of a multicopy target, but a lower accuracy. This lower accuracy can be attributed to the multicopy target. If less than the full set of 20 copies on a genome amplify, because of, for example, instability in the target copy number, than the ratio between the amplification between autosomal and gonosomal (Y) target may vary. The dynamic range of the Plexor HY kit is slightly better than that of the other kit (LaSalle et al., Forensic Science International: Genetics, "Analysis of Single and Multi-copy Methods for DNA Quantification by Real-Time Polymerase Chain Reaction"). In a statistical comparison LaSalle et al. demonstrated a significant difference between the two kits.

Another important parameter in forensics is the degradation grade of the DNA that has to be analyzed. Since the amplicon size of the Quantifiler Human and Plexor HY vary from 62 to 133 base pairs (bp), significant differences might be expected when the kits are applied to degraded DNA. Also, inhibitors must be taken into account. It may well be that DNA is present in the reaction no result is obtained due to the presence of inhibitory substances.

SUMMARY OF THE INVENTION

The present invention solves the above identified problem and provides for the following solution as outlined below.

The invention relates to a method for quantifying and/or detecting one or more nucleic acids of a genome in a sample, wherein in an amplification reaction, (a) a first nucleic acid is amplified, the locus that is amplified is a multicopy locus (MCL) within the genome, wherein the locus shares at least 80% sequence identity to a sequence according to SEQ ID NO:1 over a stretch of 80 base pairs, and wherein, the multicopy locus has copies on at least two different chromosomes, (b) a second nucleic acid that has been added as an internal control is also amplified, and (c) the amount of amplification product from the amplification of the first nucleic acid is determined.

The invention also relates to a primer and primer pair for amplifying the first nucleic acid (MCL).

Further, the invention relates to a primer and primer pair for amplifying the second nucleic acid (IC).

Further, the invention relates to a primer and primer pair for amplifying the third nucleic acid (MCL-Y)

These may be in a kit. Hence, the invention also relates to a kit for detecting and/or quantifying human nucleic acids Herein, the first nucleic acid is a multicopy locus as outlined in more detail below and often referred to as "MCL".

Herein, the second nucleic acid is an internal control as outlined in more detail below and is often referred to as "IC".

Herein, the third nucleic acid is a multicopy locus on the Y-chromosome as outlined in more detail below and is often referred to as "MCL-Y".

DETAILED DESCRIPTION OF THE INVENTION

As outlined above the quantification and detection of human DNA is difficult. Often, inhibitory substances lead to a negative PCR result, even though an adequate amount of DNA for amplification would actually be present in the sample.

The present invention solves this problem. It relates to a method for quantifying and/or detecting one or more nucleic acids of a genome in a sample, wherein in an amplification reaction, (a) a first nucleic acid is amplified, the locus that is amplified is a multicopy locus (MCL) within the genome, wherein the locus shares at least 80% sequence identity to a sequence according to SEQ ID NO:1 over a stretch of 80 base pairs, and wherein, the multicopy locus has copies on at least two different chromosomes, (b) a second nucleic acid that has been added as an internal control is also amplified, and (c) the amount of amplification product from the amplification of the first nucleic acid is determined.

Astonishingly, the inventors have found that multicopy loci that are not a repetitive element are superior to other loci when used for detection and/or quantification of nucleic acids. It is well known, that repetitive elements may vary in copy number between individuals. In general, these nucleic acids may have any origin, prokaryotic, eukaryotic or the like. Preferably they are mammalian and more preferably human. This is because one great advantage of the present invention is its application in the field of forensics.

One such sequence is identified in SEQ ID NO:1. The inventors have astonishingly found that this sequence and/or sequences that share sequence similarity with it may be found many times in the human genome.

The sequences distributed throughout the genome are not all exactly identical. It is important that the selected primers bind also to the nearly identical sequences. Thus, ideally the locus shares at least 60%, 70%, 80%, 90% or even 95% or 98% sequence identity to a sequence according to SEQ ID NO:1 over a stretch of 80 base pairs.

The determination of percent identity between two sequences is accomplished using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program, score=100, word length=12, to obtain nucleotide sequences homologous SEQ ID NO. 1. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

It is an aspect of the invention that multiple copies are amplified. Ideally, at least 4, 5, 6, 7, 8, 9, 10, 11, 12, 13, 14, 15, 16, 17, 18, 19, 20, 21, 22, 23, 24, 25, 26, 27, 28, 29 copies on various chromosomes are amplified. SEQ ID NO:1 or sequences very similar thereto are present 29 times in the human genome. This is not just astonishing but provides for the power of the present method. Also, the copies may be found on various chromosomes such as 1, 4, 5, 7, 11, 16.

It is important to note, that SEQ ID NO:1 like sequences as defined herein and/or SEQ ID NO:15 like sequences as defined herein may be used in the method according to the invention. The preferred embodiments outlined below for the method using the SEQ ID NO:1 sequence all apply likewise to the SEQ ID NO:15 sequence. Preferably they are used together in one method.

It is important to note, that SEQ ID NO. 1 like sequences as defined herein and/or SEQ ID NO. 15 like sequences as defined herein may be used in the method according to the invention. The preferred embodiments outlined below for the method using the SEQ ID NO. 1 sequence all apply likewise to the SEQ ID NO. 15 sequence. Preferably they are used together in one method.

Multi-Copy Locus on the Y-Chromosome:

Astonishingly, the inventors have also found that multicopy loci on the Y-chromosome are superior to other loci when used for detection and/or quantification of nucleic acids, because the sensitivity of the reaction can be enhanced. This is because one great advantage of the present invention is its application in the field of forensics.

One such sequence is identified in SEQ ID NO:15. The inventors have astonishingly found that this sequence and/or sequences that share sequence similarity with it may be found many times on the Y-chromosome.

The invention relates also to a method for quantifying and/or detecting one or more nucleic acids of a genome in a sample, wherein in an amplification reaction, a. a first nucleic acid is amplified, the locus that is amplified is a multicopy locus on the Y chromosome (MCL) within the genome, wherein the locus shares at least 80% sequence identity to a sequence according to SEQ ID NO:15 over a stretch of 80 base pairs, b. a second nucleic acid that has been added as an internal control (IC) is also amplified, c. the amount of amplification product from the amplification of the first nucleic acid is determined.

The sequences distributed throughout the Y-chromosome are not all exactly identical. It is important that the selected primers bind also to the nearly identical sequences. Thus, ideally the locus shares at least 60%, 70%, 80%, 90% or even 95% or 98% sequence identity to a sequence according to SEQ ID NO:15 over a stretch of 80 base pairs.

The forensic workflow of sexual assault samples suggests the quantification of the male DNA before the STR reaction is carried out. This is done first to help in the decision of which kind of STR Kit has to be used for the genetic analysis, and then to determine how much DNA was obtained from a sample, e.g. collected from a crime scene, and how much of this DNA should be used in a STR reaction. Different STR Kits are available, the typical STR Kit detects genetic length polymorphisms on different autosomal chromosomes, but in some cases, such as with sexual assault samples, the analysis of length polymorphisms exclusively on the Y-chromosome could be advantageous, because the female DNA doesn't have a Y chromosome.

The typical STR reaction works optimally in certain range of template DNA and the whole analysis is very labor-intensive, therefore methodologies are needed that ensure a very high success rate in the STR analysis. Therefore, it is a real advantage if the quantification kit enables the user not only to surely identify the amount of DNA present but also to assess the absence of inhibitors, which could compromise the STR reaction result, which would result in failure or loss of valuable sample material, which could be further purified in case critical inhibition is observed.

Ideally, the amplification product of the third nucleic acid (MCL-Y) is between 60 base pairs and 200 base pairs long, between 80 and 300, between 100 and 200 or between 120 and 180 base pairs.

In a preferred embodiment, the third nucleic acid (MCL-Y) is about 130 base pairs in length (+/−20%).

One feature of the invention is a novel internal control (IC) for detection of PCR inhibitors. The IC is co-amplified in parallel in the same reaction vial with one or more specific targets. The IC is used to detect PCR inhibitors in the reaction. Hence, inhibition of the IC, detectable by a shift in the threshold cycle in real-time PCR, is a marker for the presence of certain amounts of PCR inhibitors in the reaction.

The forensic workflow suggests the quantification of the DNA before the STR reaction is carried out. This is done to determine how much DNA was obtained from a sample, e.g. collected from a crime scene, and how much of this DNA should be used in a STR reaction. The typical STR reaction works optimally in certain range of template DNA and the whole analysis is very labor-intensive, therefore methodologies are needed that ensure a very high success rate in the STR analysis. Therefore, it is a real advantage if the quantification kit enables the user not only to surely identify the amount of DNA present but also to assess the absence of inhibitors, which could compromise the STR reaction result, which would result in failure or loss of valuable sample material, which could be further purified in case critical inhibition is observed.

In the present invention, the nature of the IC is astonishingly such that it fits to the recent forensic workflows by reporting the presence of inhibitors, but still giving a good quantification result, providing a stable Ct value of internal control over the whole DNA concentration range when inhibitors are present at uncritical level, and has a high correlation level of inhibitors critical for the STR reaction. Some of the new generation of STR kits recently introduced in the market demonstrate increased inhibitor resistance as kits introduced earlier. These new STR kits have been further developed to provide higher resistance to PCR inhibitors, which also provides new requirements to the DNA quantification methodology, by providing an IC that only reports levels of inhibition that are significant for the success of the subsequent STR reaction.

The IC of the present invention carries a control DNA sequence that does not occur in the sample nucleic acid, allowing the selection of oligonucleotide primers and/or probes that specifically only detect the IC.

In a preferred embodiment, the IC is a PCR product or a plasmid carrying the control DNA sequence. Alternatively, the IC could also be a synthetic longmer, or a plasmid or any other kind of vector.

In a preferred embodiment also the amount of amplification product of the second nucleic acid is determined.

The amplification method is either a non-isothermal method or an isothermal method.

The non-isothermal amplification method may be selected from the group of polymerase chain reaction (PCR) (Saiki et al. (1985) Science 230:1350), quantitative real-time PCR (rt-PCR), ligase chain reaction (LCR) (Landegren et al. (1988) Science 241:1077-1080). Polymerase chain reaction amplification is preferred.

The isothermal amplification method may be selected from the group of helicase-dependent amplification (HDA) (Vincent et al. (2004) EMBO rep 5(8):795-800), thermostable HDA (tHDA) (An et al. (2005) J Biol Chem 280(32):28952-28958), strand displacement amplification (SDA) (Walker et al. (1992) Nucleic Acids Res 20(7):1691-6), multiple displacement amplification (MDA) (Dean et al. (2002) Proc Natl Acad Sci USA 99(8): 5261-5266), rolling-circle amplification (RCA) (Liu et al. (1996) J Am Chem Soc 118:1587-1594), restriction aided RCA (Wang et al. (2004) Genome Res 14:2357-2366), single primer isothermal amplification (SPIA) (Dafforn et al. (2004) Biotechniques 37(5):854-7), transcription mediated amplification (TMA) (Vuorinen et al. (1995) J Clin Microbiol 33: 1856-1859), nicking enzyme amplification reaction (NEAR) (Maples et al. US2009017453), exponential amplification reaction (EXPAR) (Van Ness et al. (2003) Proc Natl Acad Sci USA 100 (8):4504-4509), loop mediated isothermal amplification (LAMP) (Notomi et al. (2000) Nucleic Acids Res 28(12): e63), recombinase polymerase amplification (RPA) (Piepenburg et al. (2006) PloS Biol 4(7):1115-1120), nucleic acid sequence based amplification (NASBA) (Kievits et al. (1991) J Virol Methods 35:273-286), smart-amplification process (SMAP) (Mitani et al. (2007) Nat Methods 4(3):257-62).

By "isothermal amplification reaction" in context of the present invention it is meant that the temperature does not significantly change during the reaction. In a preferred embodiment the temperature of the isothermal amplification reaction does not deviate by more than 10° C., preferably by not more than 5° C., even more preferably not more than 2° C. during the main enzymatic reaction step where amplification takes place.

Depending on the method of isothermal amplification of nucleic acids different enzymes are required for the amplification reaction. Known isothermal methods for amplification of nucleic acids are the above mentioned, wherein the at least one mesophilic enzyme for amplifying nucleic acids under isothermal conditions is selected from the group consisting of helicase, mesophilic polymerases, mesophilic polymerases having strand displacement activity, nicking enzymes, recombination proteins, ligases, glycosylases and/or nucleases.

"Helicases" are known by those skilled in the art. They are proteins that move directionally along a nucleic acid phosphodiester backbone, separating two annealed nucleic acid strands (e.g. DNA, RNA, or RNA-DNA hybrid) using energy derived from hydrolysis of NTPs or dNTPs. Based on the presence of defined helicase motifs, it is possible to attribute a helicase activity to a given protein. The skilled artisan is able to select suited enzymes with helicase activity for the use in a method according to the present invention. In a preferred embodiment the helicase is selected from the group comprising helicases from different families: superfamily I helicases (e.g. dda, perA, F-plasmid traI protein helicase, uvrD), superfamily II helicases (e.g. recQ, NS3-helicase), superfamily III helicases (e.g. AAV rep Helicase), helicases from DnaB-like superfamily (e.g. T7 phage helicase) or helicases from Rho-like superfamily.

The amplification methods will comprise buffers, dNTPs or NTPs in addition to the enzymes required.

As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescent label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine. Furthermore, ddNTPs of the above-described molecules are encompassed in the present invention.

As used herein, the term "NTP" refers to ribonucleoside triphosphates. Non-limiting examples of such NTPs are ATP, GTP, CTP, TTP, UTP, which may also be present in the form of labelled derivatives, for instance comprising a fluorescent label, a radioactive label, a biotin label.

In a preferred embodiment the amplification method is a polymerase chain reaction or a real-time PCR reaction and the amount of nucleic acid determined, is determined either during the amplification process or as an end point measurement at the end of the amplification reaction.

Oligonucleotide primers may be prepared using any suitable method, such as, for example, the phosphotriester and phosphodiester methods or automated embodiments thereof. In one such automated embodiment diethyl phosphoramidites are used as starting materials and may be synthesized as described by Beaucage et al. (1981) Tetrahedron Letters 22:1859-1862. One method for synthesizing oligonucleotides on a modified solid support is described in U.S. Pat. No. 4,458,006. It is also possible to use a primer, which has been isolated from a biological source (such as a restriction endonuclease digest). Preferred primers have a length of about 6-100 bases, more preferably about 20-50, most preferably about 20-40 bases. DNA Quantification using real-time PCR.

During PCR, the amount of DNA theoretically doubles with every cycle. After each cycle, the amount of DNA is twice what it was before.

The absolute amount of DNA in an unknown sample is preferably determined using the IC.

Using real-time PCR techniques, fluorescence is detected and measured in the real-time PCR thermocycler, and its geometric increase corresponding to exponential increase of the product is used to determine the threshold cycle (CT) in each reaction.

A standard curve (plot of CT value/crossing point against log of amount of standard) is generated using different dilutions of the standard. The CT value of the unknown samples is compared with the standard curve, allowing calculation of the initial amount of the target. It is important to select an appropriate standard for the type of nucleic acid to be quantified. To generate a standard curve, at least 5 different amounts of the standard should be quantified, and the amount of unknown target should fall within the range of the standard curve. Hence, in one embodiment also the above quantification steps are performed.

Ideally, the amplification product of the first nucleic acid (MCL) is between 60 base pairs and 200 base pairs long, between 80 and 300, between 100 and 200 or between 120 and 180 base pairs.

Further, ideally, the amplification product of the second nucleic acid (IC) is between 60 and 400, between 100 and 400 base pairs, between 80 and 300 base pairs or between 150 and 250 base pairs.

Astonishingly it has turned out that, if the amplification of the second nucleic acid (IC) is longer than the amplification product of the first nucleic acid (MCL) better results may be achieved.

In a preferred embodiment, the first nucleic acid (MCL) is about 140 base pairs in length (+/−20%) and the second nucleic acid (IC) is about 200 base pairs in length (+/−20%).

In a preferred embodiment, the third nucleic acid (MCL-Y) is about 130 base pairs in length (+/−20%).

Ideally, the amplification reaction comprises, (i) Tris-HCl at a pH of between 8 and 8.8 (at 20° C.) and/or, (ii) potassium salt selected from the group of, potassium chloride and potassium sulphate and/or, (iii) an ammonium salt, preferably ammonium chloride or ammonium sulphate and/or, (vi) magnesium chloride and/or, (v) a hot-start polymerase.

Preferably, the concentration of Tris-HCl is in the range from 10 to 100 mM, most preferably in the range from 20 to 70 mM, the concentration of $K^+$ is in the range from 1-25 mM, most preferred in the range from 2.5 to 20 mM, the concentration of $NH_4^+$ in range from 1 to 40 mM, most preferred in the range from 2.5 to 30 mM, and a concentration of $Mg^{2+}$ of 0.5 mM to 8 mM in excess to the concentration of the four dNTP's, most preferred a concentration of $Mg^{2+}$ of 0.7 mM to 5 mM in excess to the concentration of the four dNTP's, a hot-start polymerase, preferentially a hot-start polymerase allowing a hot-start time of less than 5 min, most preferred below 2 min.

It is important that the amount of second nucleic acid is correctly chosen. This IC is able to determine whether there is DNA in the reaction or whether possibly no reaction product is obtained due to the fact that an inhibitor is present in the reaction. A reaction typically has a volume of between 5 and 100 μl, more preferred in range from 7 μl and 75 μl, most preferred in range from 10 μl and 50 μl, ideally in range from 15 μl and 25 μl.

The inventors have found out, that between 100 and 5000 copies of the second nucleic acid (IC) are ideal. Preferably between 200 and 2000 copies are present, more preferably between 500 and 1500 copies, more preferably 1000 copies (+/−20%). The amount in μg/μl depends on the size/length of nucleic acid. Preferably the nucleic acid is a PCR product or plasmid DNA.

The invention also relates to a primer for amplifying the first nucleic acid (MCL) selected from the group of

```
                                       (SEQ ID NO: 12/4N-S1C Pr)
a.   5'-CCGGGAAGCAGAAGGTGG-3'

(SEQ ID NO: 11/4N-S1C)
b.   5'-Fam-CGAGCTCAGTTGTGCCTGTAGAGCTCG-dabcyl-C18-
     ACCTCTTCCTCTTGGCTGGG-3'
```

The invention further relates to a primer pair for amplifying the first nucleic acid (MCL) consisting of the primers as follows:

```
                                       (SEQ ID NO: 12/4N-S1C Pr)
c.   5'-CCGGGAAGCAGAAGGTGG-3'

(SEQ ID NO: 11/4N-S1C)
d.   5'-Fam-CGAGCTCAGTTGTGCCTGTAGAGCTCG-dabcyl-C18-
     ACCTCTTCCTCTTGGCTGGG-3'
```

The invention further relates to a primer for amplifying the second nucleic acid (IC) selected from the group of

```
                                       (SEQ ID NO: 13/AT-IC_Rev.)
e.   5'-GCTATCCAGTGTGCCTAGGCAA-3'

(SEQ ID NO: 14/AT-IC_Yak)
f.   5'-YAK-TGGCGTAGTCGTTCAACGCCA/Dabcyl/HEG/CCACGA
     GCGTACTTCGACTGAA-3'
```

The invention also relates to a primer pair for amplifying the second nucleic acid (IC) consisting of:

```
                                       (SEQ ID NO: 13/AT-IC_Rev.)
g.   5'-GCTATCCAGTGTGCCTAGGCAA-3'

(SEQ ID NO: 14/AT-IC_Yak)
h.   5'-YAK-TGGCGTAGTCGTTCAACGCCA/Dabcyl/HEG/CCACGA
     GCGTACTTCGACTGAA-3'
```

The invention also relates to a primer for amplifying the third nucleic acid (MCL-Y) selected from the group of:

a. 5'-TGGCTGAGTTCCTCCACCTG-3' (SEQ ID NO: 37; MCL-Y Pr)

b. 5'-Quasar670-cgaccgtgaagcatgcgtttcggtcg-BHQ2-C18-agtgggagagctgggaa-3' (SEQ ID NO: 38/MCL-Y Scorp)

Note, herein in all cases where a Scorpion primer is depicted (Scorp) as above for SEQ ID NO:38 the priming part of the primer is the 3'-prime part and the invention relates in such a case preferably to this part and not the probe part (agtgggagagctgggaa-3') (nucleotides 27-43 of SEQ ID NO:38).

Further, the invention relates to a kit for detecting and/or quantifying human nucleic acids, wherein the kit comprises one or more primers that, under stringent conditions, binds a sequence that shares at least 80% sequence identity to a sequence according to SEQ ID NO:1 over a stretch of 80 base pairs and, at least one primer or probe that stringently binds the second nucleic acid (IC), or comprises a primer or primer pair according to those outlined above.

Ideally, the kit has at least one primer that has a nucleotide sequence that differs from SEQ ID NO:2, 3, 5, 6, 8, 9, 10, 11 and/or 12 and/or SEQ ID NO:37 and/or 38 by no more than 5 nucleotides over a stretch of 18 nucleotides. Ideally, the kit has a nucleotide sequence that differs from SEQ ID NO:2, 3, 5, 6, 8, 9, 10, 11 and/or 12 and/or SEQ ID NO:37 and/or 38 by no more than 5 nucleotides over a stretch of 18 nucleotides.

FIGURE CAPTIONS

FIG. 1

Figure 1:
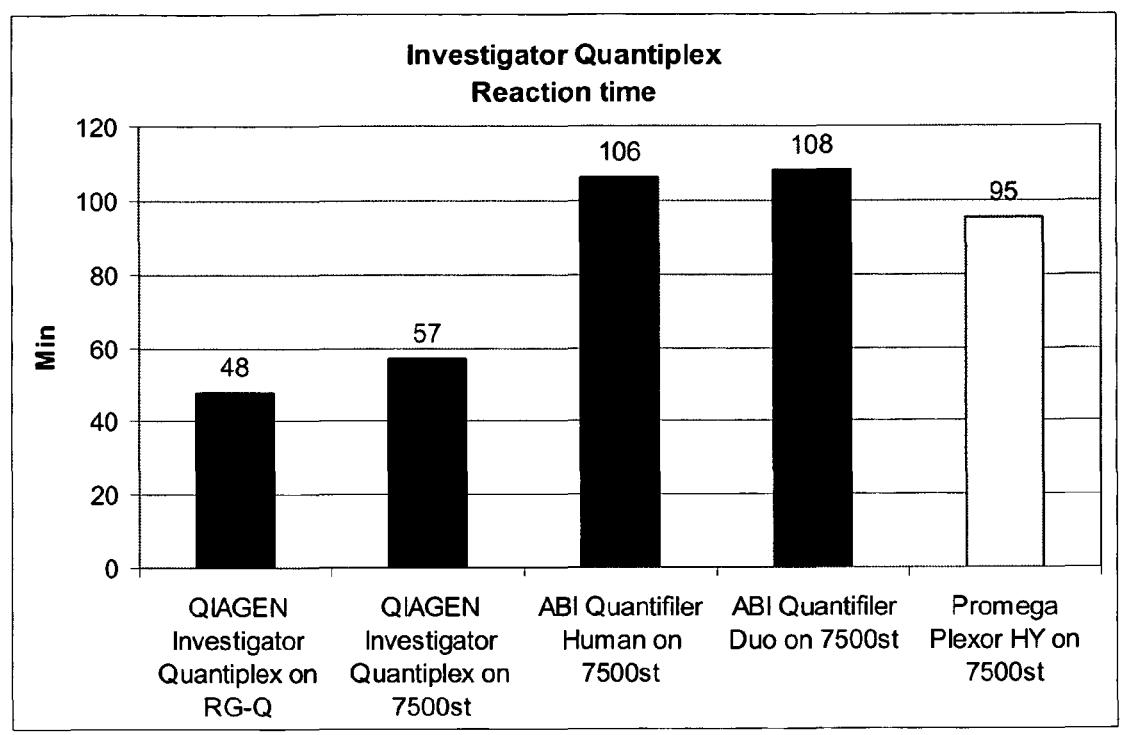

FIG. 1 demonstrates the advantages of the invention by minimized reaction time. The "Qiagen Investigator Quantiplex" stands for a special embodiment of the method in scope of the invention. The first column (from left) shows the run time of the Qiagen Investigator Quantiplex" method on the Rotor-Gene Q real-time PCR instrument (Qiagen). Column 2 show the run time of the "Qiagen Investigator Quantiplex" method on the 7500 Fast PCR System from Applied Biosystems. For comparison, column 3 shows the run time for the Quantifier Human Kit from Applied Biosystems, run on the 7500 Real-time PCR System from Applied Biosystems, column 4 shows the run time for the Quantifier Duo Kit from Applied Biosystems run on the 7500 Real-time PCR System from Applied Biosystems, and column 5 shows the run time for the Plexor HY Kit from Promega, run on the 7500 Real-time PCR System from Applied Biosystems.

FIG. 2

Figure 2:
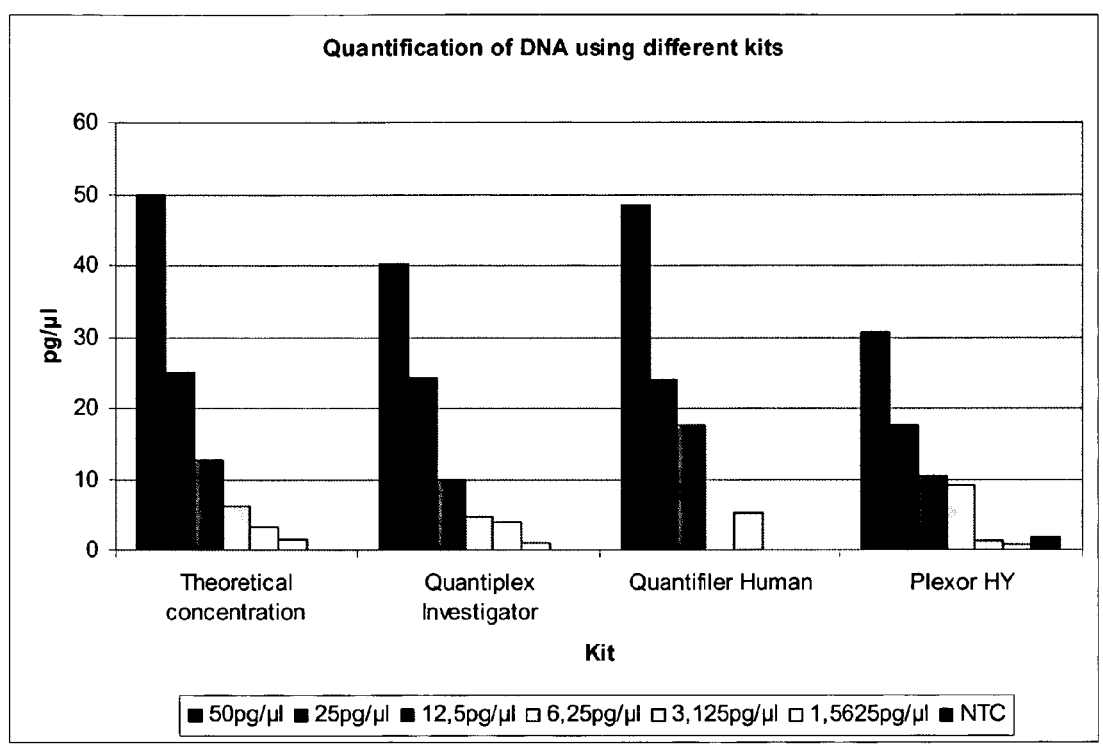

FIG. 2 shows a comparison of the accuracy of the different quantification methods in relation to the theoretical concentration. "Quantiplex Investigator" stands for a special embodiment of the method in scope of the invention. The commercially available quantification kits were set up and analyzed as described in the appropriate handbook. A serial dilution of human reference DNA (obtained from National Institute of Standards and Technology, USA) at known concentration was used as a template for all of the three kits. The "Quantiplex Investigator" method provides high accuracy to quantify all amounts of used template at their correct concentrations with a maximum error of 20%, especially the concentrations of 6.25 pg/µl and below were much more adequately quantified compared to the Quantifier Human method (based on Quantifier Human Kit from Applied Biosystems), which uses a single copy target, and the Plexor HY method (based on Plexor HY Kit from Promega), which uses a target present at few copies, reference given in description. Quantifier Human method (based on Quantifier Human Kit from Applied Biosystems which uses a single copy target) showed high fluctuations or even failed to generate a quantification result at and below 12.5 pg/µl human DNA. The Plexor HY shows high deviations from the theoretical quantification results. 2 µl of given dilutions of the human reference DNA were used in each reaction. Concentrations refer to the concentration in the template solution. NTC: no template control.

FIG. 3

Figure 3:
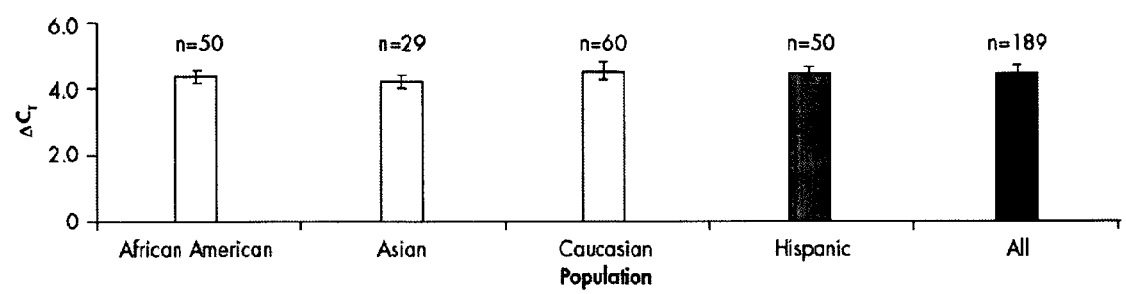

FIG. 3 shows no copy-number variation of the human marker detected by SEQ ID NO:11 and SEQ ID NO:12 in genomic DNA samples from donors of different ethnic groups. A quantitative real-time PCR was run using to compare a human specific single-copy target and the Investigator Quantiplex multi-copy target. The ΔCT between the two targets is shown for the different populations. It becomes visible that the ΔCT is constant in all populations, demonstrating a constant copy number of the region detected by SEQ ID NO:11 and SEQ ID NO:12.

FIG. 4

Figure 4:
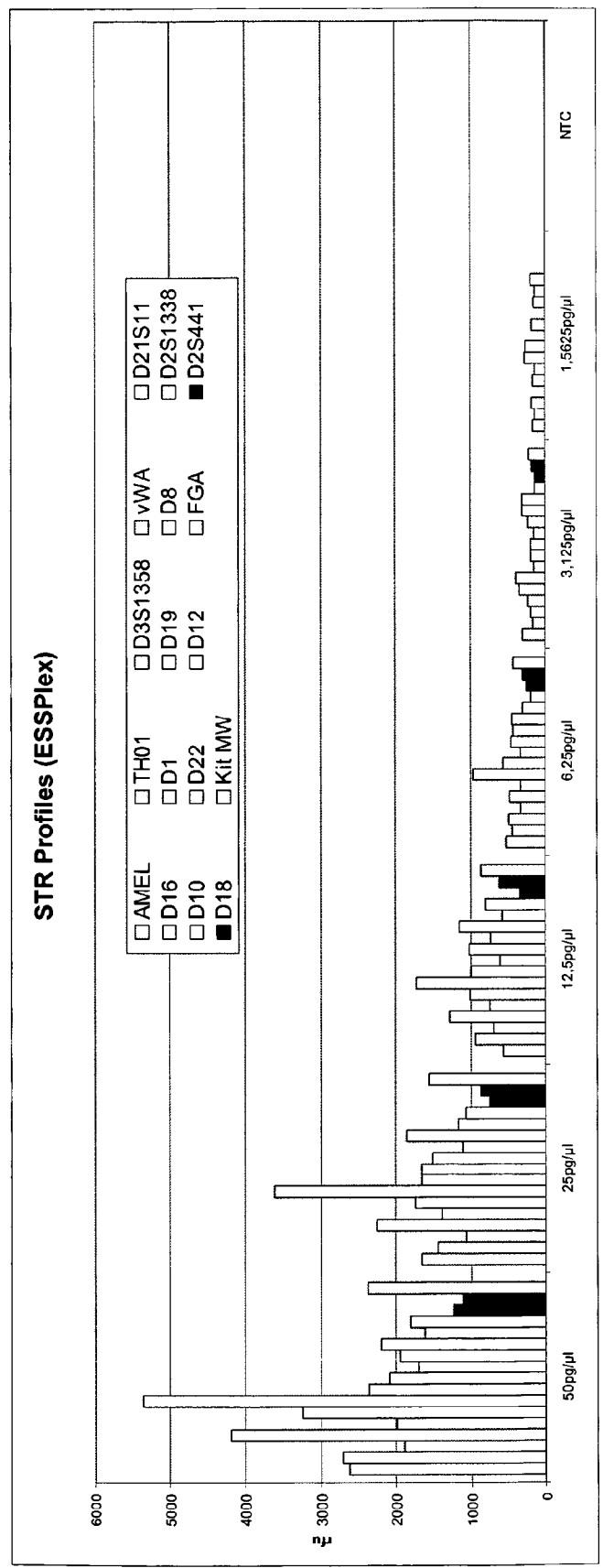

FIG. 4 shows the importance of high sensitivity and correct quantification (shown in FIG. 2) by means of STR analysis following the quantification reaction. In FIG. 4 the serial dilution of human DNA from FIG. 2 was used to generate the shown STR profiles following the protocol for the Investigator ESSplex Kit (Qiagen). It demonstrates the possibility to obtain a complete STR profile even from the lowest concentration used in FIG. 2, demonstrating the usefulness of highly accurate quantification even of low template amounts.

FIG. 5

Figure 5:
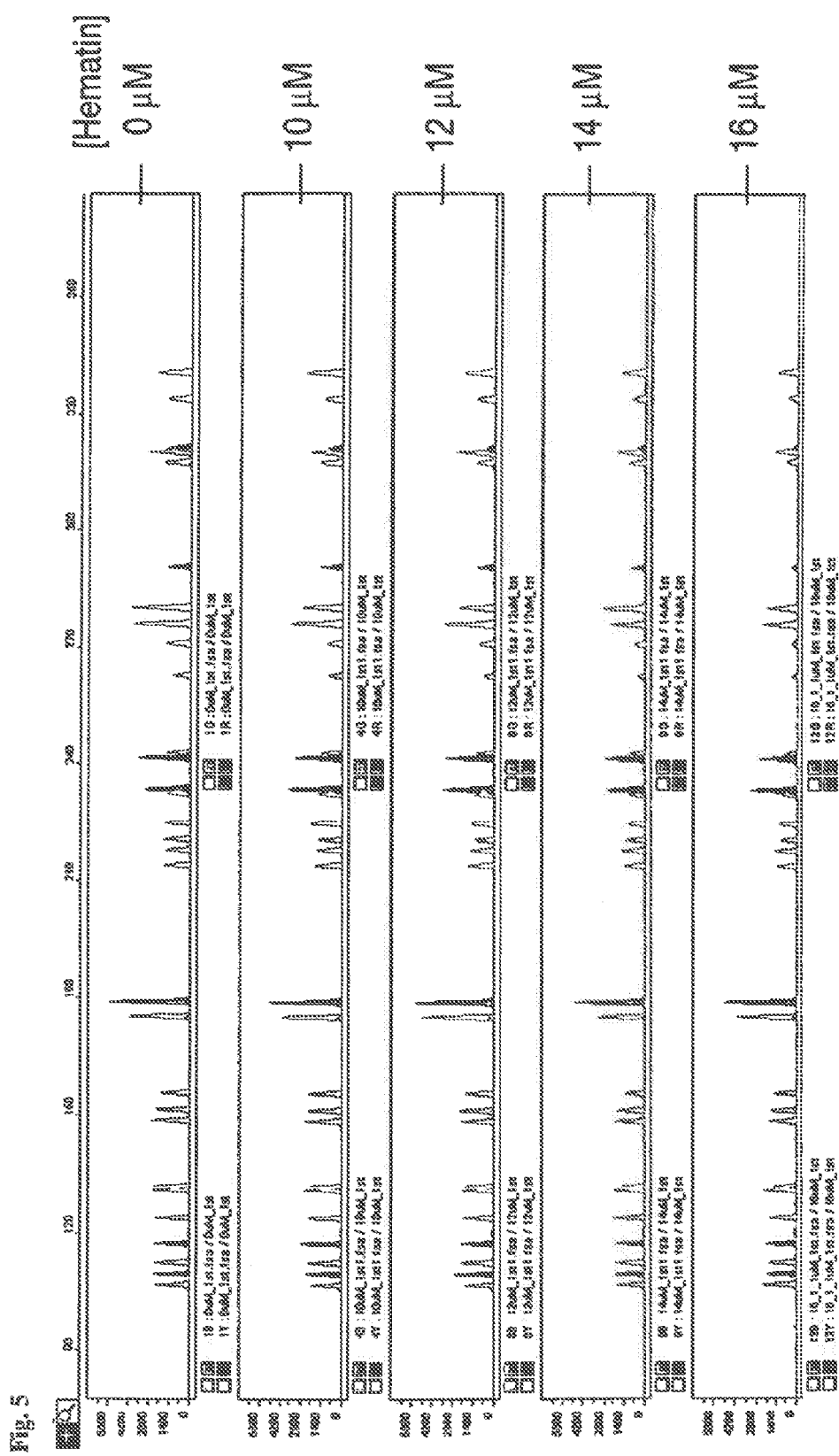
Figure 5:
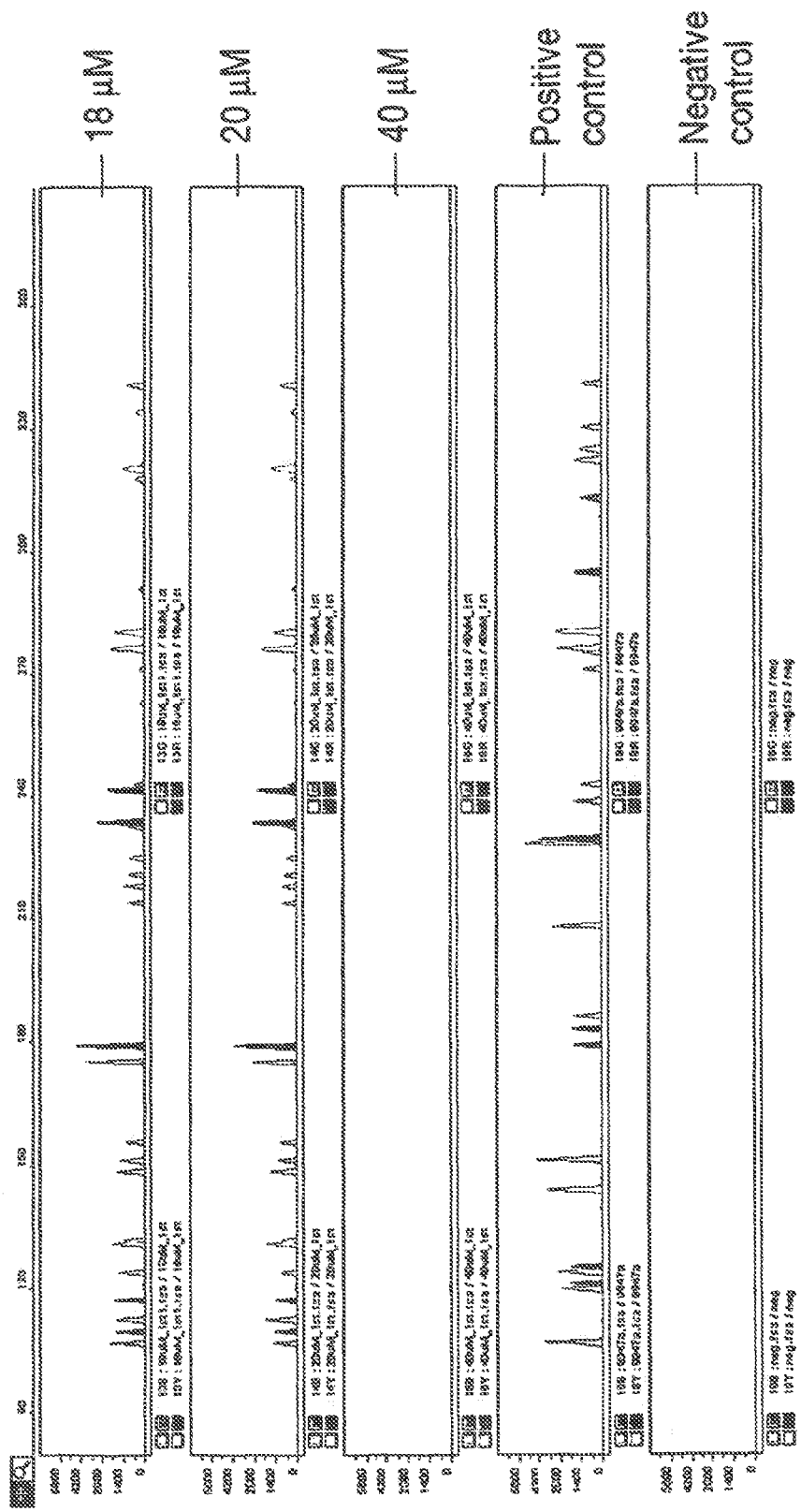

FIG. 5 shows a dataset from the literature on the inhibition of the AmpF1STR Identiler reaction by hematin, Using Identifier (taken from the source indicated below—Quantifier Human page 137) the DNA fingerprinting reaction works till a hematin concentration up to 20 µM.

Source: www3.appliedbiosystems.com/cms/groups/applied_markets_support/documents/generaldocuments/cms_041395.pdf

FIG. 6

FIG. 6 shows a dataset from the literature on the inhibition of the AmpF1STR NGM Kit. This is a so-called "next generation STR-Kits", which are much more resistant to the presence of inhibitors, in the example below up to 75 µM hematin.

Source: marketing.appliedbiosystems.com/images/All_Newsletters/Forensic_0710/pdfs/Customer-Corner/next-Generation.pdf

FIG. 7

FIG. 7 shows an example of inhibitor sensitivity in quantification reactions. Data are taken from the developmental validation reports of the commercial kits Quantifier Human and Y. Data are available in the validation report of the kit supplier, at:

Quantifier Human www3.appliedbiosystems.com/cms/groups/applied_markets_suppor-t/documents/general documents/cms_041395.pdf Quantifier Duo www.appliedbiosystems.com.br/site/material/5q7aqqbm.pdf The forensic workflow suggests the quantification of the DNA before the STR reaction is carried out. This is done to determine how much DNA was obtained from a sample, e.g. collected from a crime scene, and how much of this DNA should be used in a STR reaction. The typical STR reaction works optimally in certain range of template DNA and the whole analysis is very labor-intensive, therefore methodologies are needed that ensure a very high success rate in the STR analysis. Therefore, it is a real advantage if the quantification kit enables the user not only to surely identify the amount of DNA present but also to assess the absence of inhibitors, which could compromise the STR-reaction result, which would result in failure or loss of valuable sample material, which could be further purified in case critical inhibition is observed.

The data show that only the combined Quantifier Human and Y kit show a slightly lower stability of the Internal Control target in comparison to the human target. In this case, the Ct value of the IC shifts to higher values when an inhibitor is contained in the DNA sample, while the Ct value of the Human and the Y kits remain stable, at least for smaller amounts of hematin. In the case of the Quantifier human and Y Kits the resistance to inhibitors such as hematin is quite little (between 16 μM and 20 μM hematin in the reaction). Hence, methodologies are missing that are compatible with higher amounts of inhibitor resistance as required for the next generation of STR kits.

FIG. 8

FIG. 8 shows an example of inhibitor sensitivity in quantification reactions. Data are taken from the developmental validation reports of the commercial kit Quantifier Duo Data are available in the validation report of the kit supplier, at:

Quantifiler Duo www.appliedbiosystems.com.br/site/material/5q7aqqbm.pdf

The internal control system in the Quantifier Duo Kit is more stable than the human specific target in the presence of inhibitors. The utility of the internal control system in this case is of course low because the internal control system doesn't give any indication of the presence of inhibitors in the sample while the DNA quantification is already compromised. In fact, the Ct values of the RPPH1 and of the SRY systems shift to higher values even at low amounts of inhibitors. The dramatic increase of the Ct value of the RPPH1 system to >40 in the presence of 12.5 μM hematin makes the quantification of the human DNA impossible.

The resistance to the presence of inhibitors in the sample is very low in comparison to the new generation STR-kits (i.e. 10 μM hematin and 3.75 ng/μl humic acid).

FIG. 9

Figure 9:
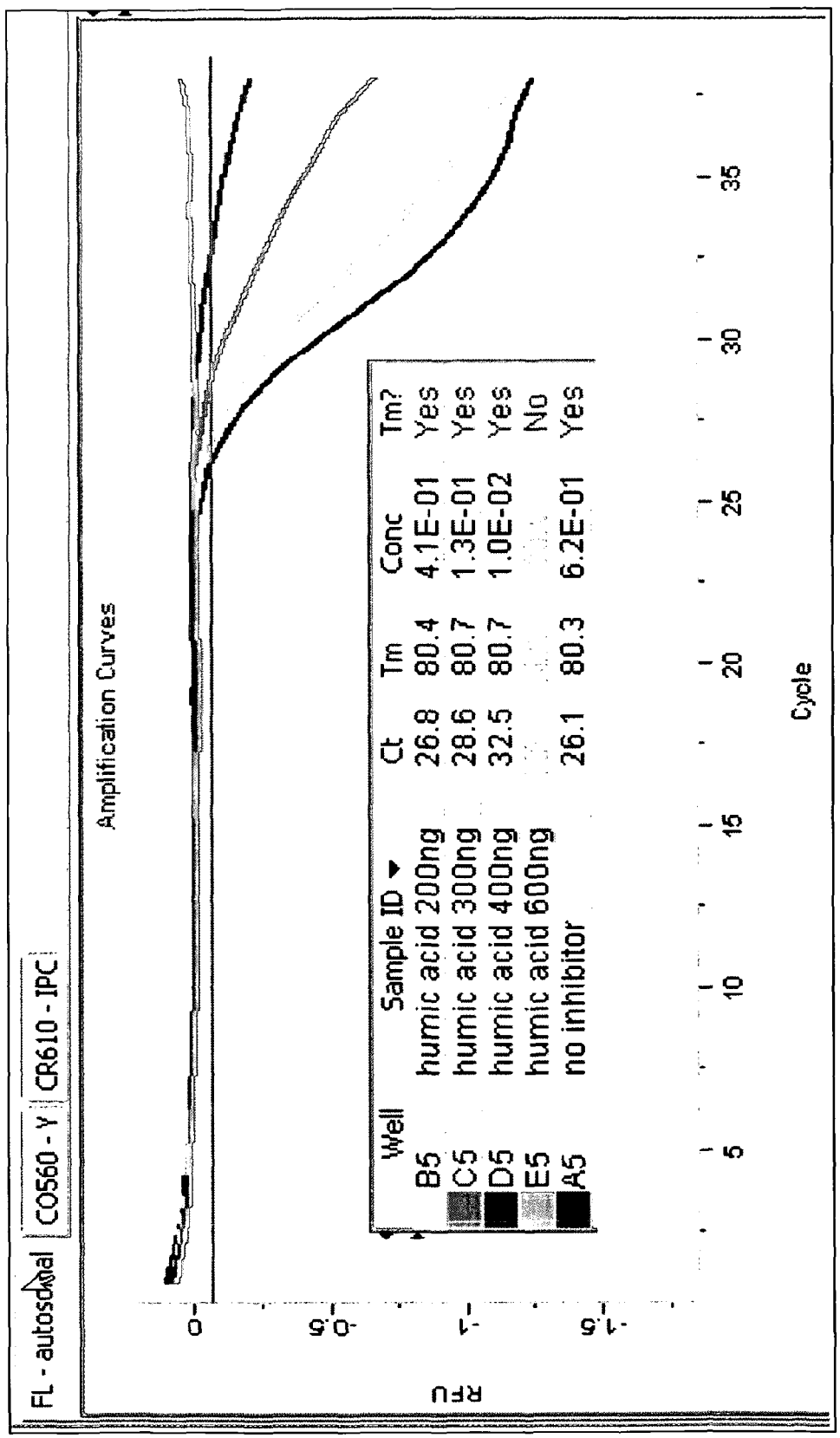
Figure 9:
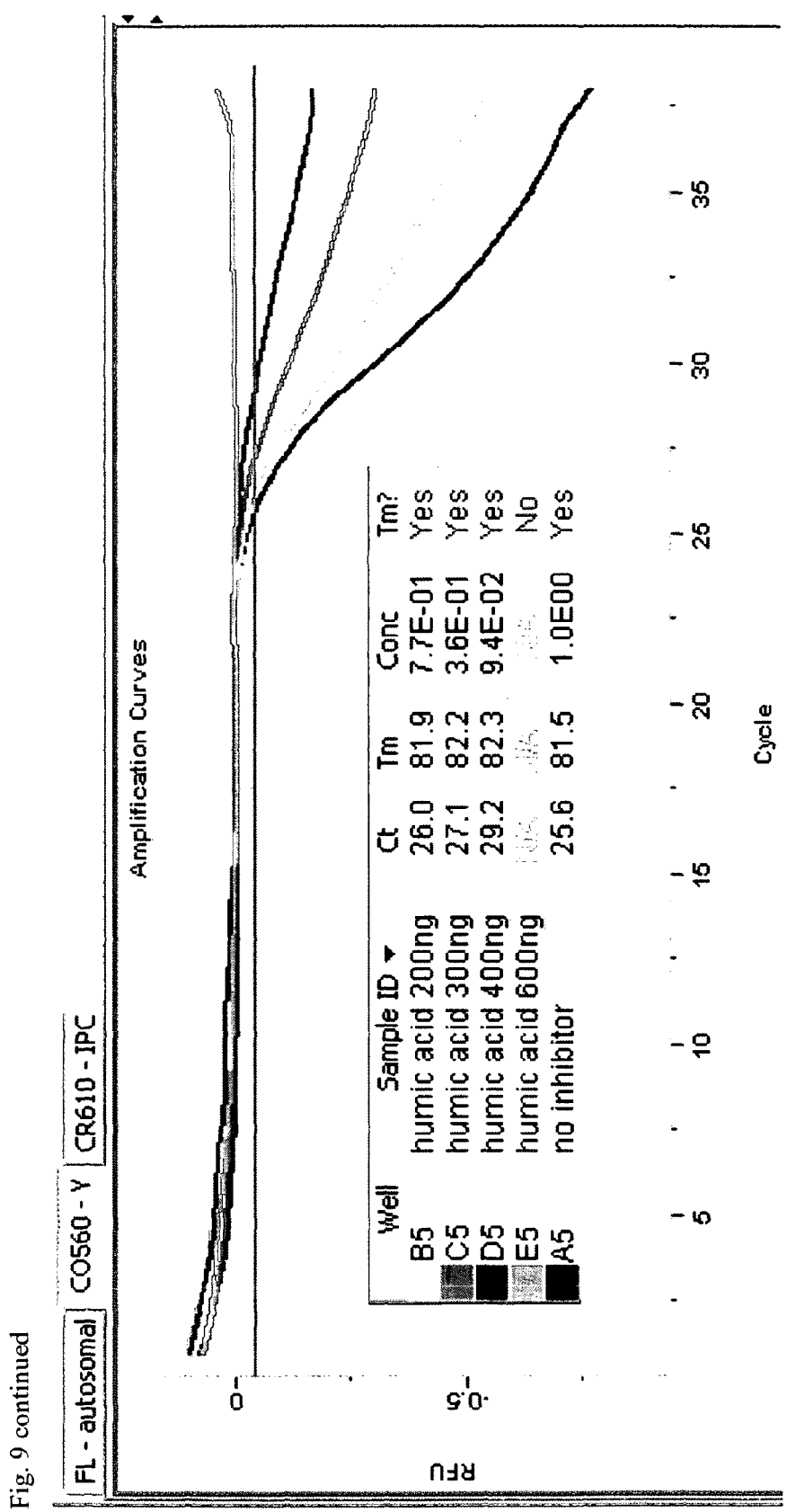

FIG. 9 shows an example of inhibitor sensitivity in quantification reactions. Data are taken from the developmental validation reports of the commercial kit Plexor HY. Data are available in the validation report of the kit supplier, at:

Plexor HY www.promega.com/plexorhy/an157.pdf

The Plexor HY Kit shows quite the same stability of the Internal Control target in comparison to the human target, as visible by a comparable shift of the Ct to higher values for the autosomal target (upper panels) and the Internal control (IPC) shown in the lower panels. In this case, the Ct value of the IC shifts to higher values when an inhibitor is contained in the DNA sample. Even the Ct value of the human specific target shifts to higher levels when the inhibitor is contained in the sample, thus compromising the DNA quantification. In the case of the Plexor HY the resistance to inhibitors such as hematin is quite little (ca. 25 μM hematin in the reaction).

FIG. 10

Figure 10:
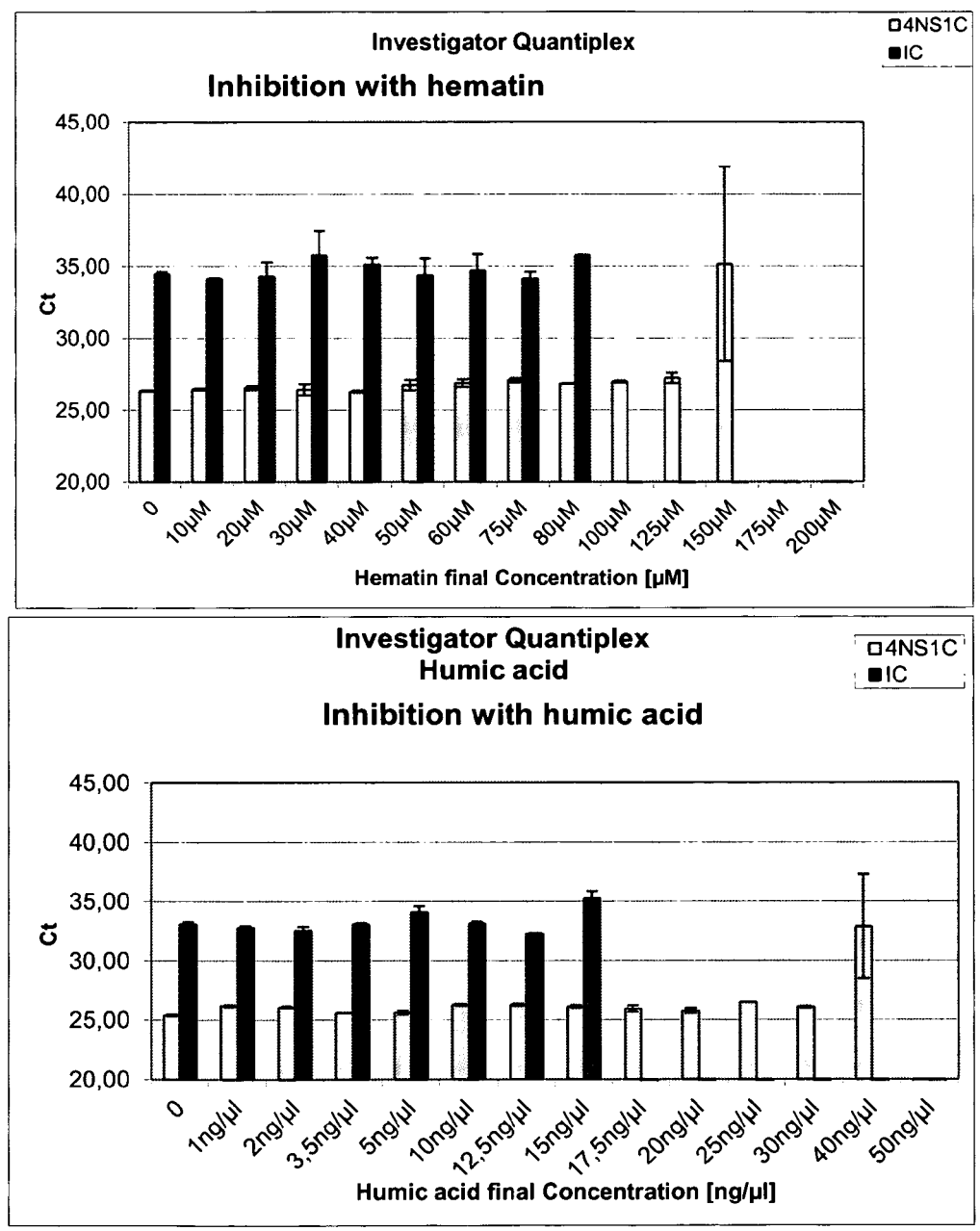

FIG. 10 shows result of a reaction in scope of the invention in presence of the given concentrations of the PCR inhibitors Humic Acid and Hematin.

Through the use of the invention a high stability of the internal control to higher concentrations of inhibitors and a higher stability of the human specific target could be achieved. This gives accurate quantification even if the internal control is completely inhibited. The inhibition of the human specific target starts at a concentration between 80 and 100 μM hematin, which perfectly fits the inhibitor resistance of the Next generation STR-Kits like AmpF1STR NGM from Applied Biosystems or Investigator ESSplex from Qiagen.

FIG. 11

Shows the Sequence Listing

FIG. 12

Figure 12:
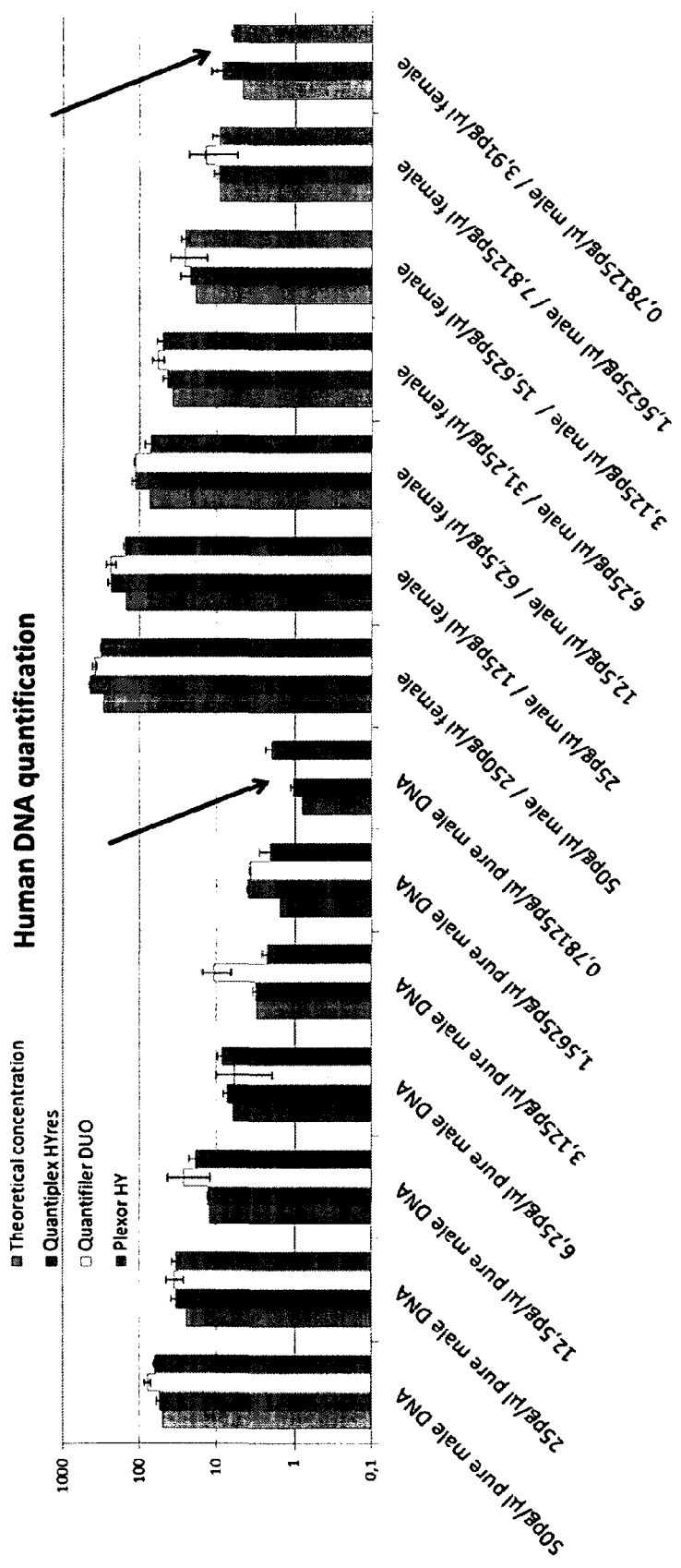
Figure 12:
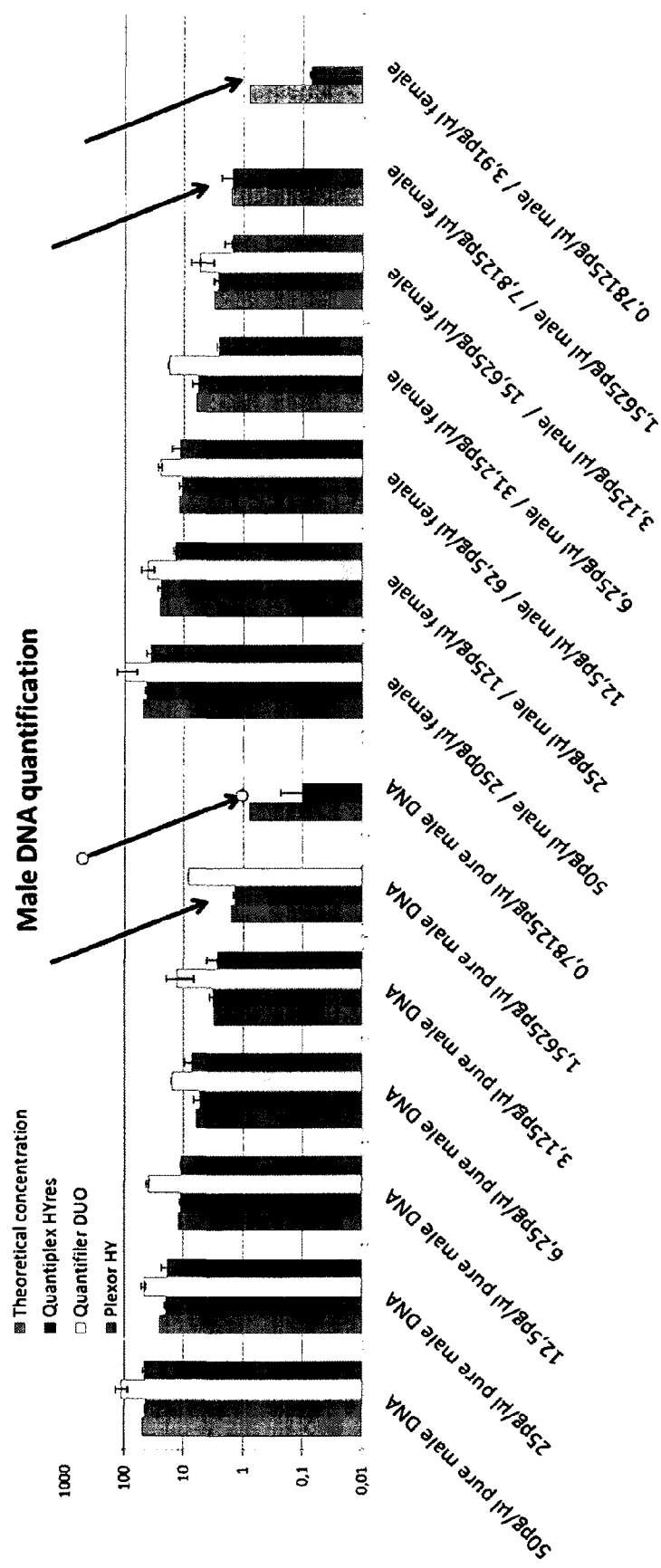

FIG. 12 shows a comparison of the accuracy of the different quantification methods in relation to the theoretical concentration. "Quantiplex Investigator HYres" stands for a special embodiment of the method in scope of the invention. The commercially available quantification kits were set up and analyzed as described in the appropriate handbook. A serial dilution of human DNAs (isolated from human blood from anonymous donors using the QIAamp Investigator Kit) and mixtures thereof at known concentrations was used as a template for all of the three kits. The "Quantiplex Investigator HYres" method provides high accuracy to quantify all amounts of used template at their correct concentrations, especially the concentrations of 6.25 pg/μl and below were much more adequately quantified compared to the Quantifiler DUO method (based on Quantifiler DUO Kit from Applied Biosystems), which uses a single copy target, and the Plexor HY method (based on Plexor HY Kit from Promega), which uses a target present at few copies, reference given in description. Quantifiler DUO method (based on Quantifier DUO Kit from Applied Biosystems which uses a single copy target) showed high fluctuations or even failed to generate a quantification result at and below 1.5 pg/μl human DNA and failed to quantify male DNA concentrations below 1.5 pg/μl in the presence of female DNA background. The Plexor HY failed to quantify the male DNA fraction below 3 pg/μl in the presence or absence of background female DNA. 2 μl of given dilutions of the human reference DNA were used in each reaction. Concentrations refer to the concentration in the template solution.

FIG. 13

Figure 13:
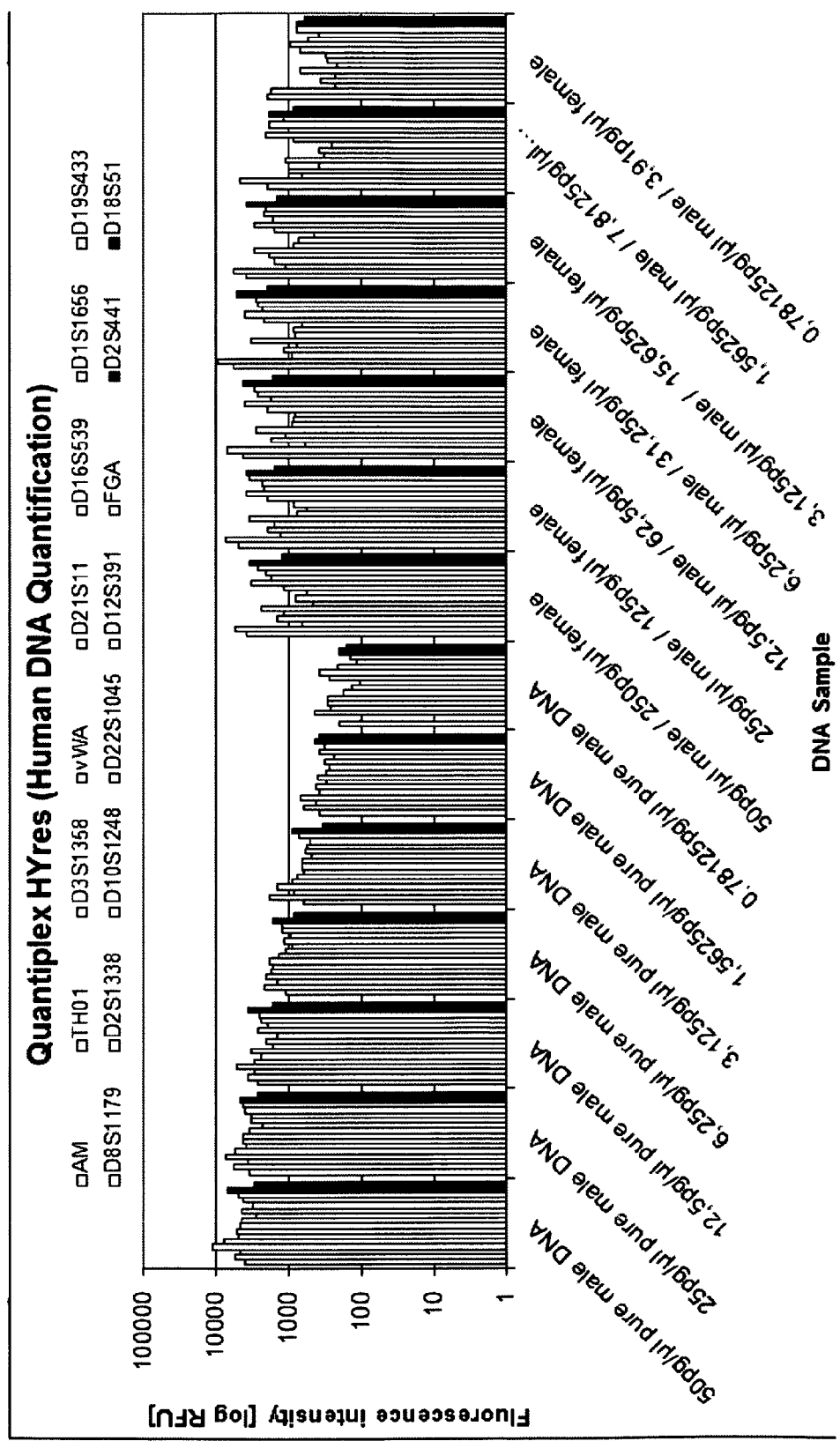
Figure 13:
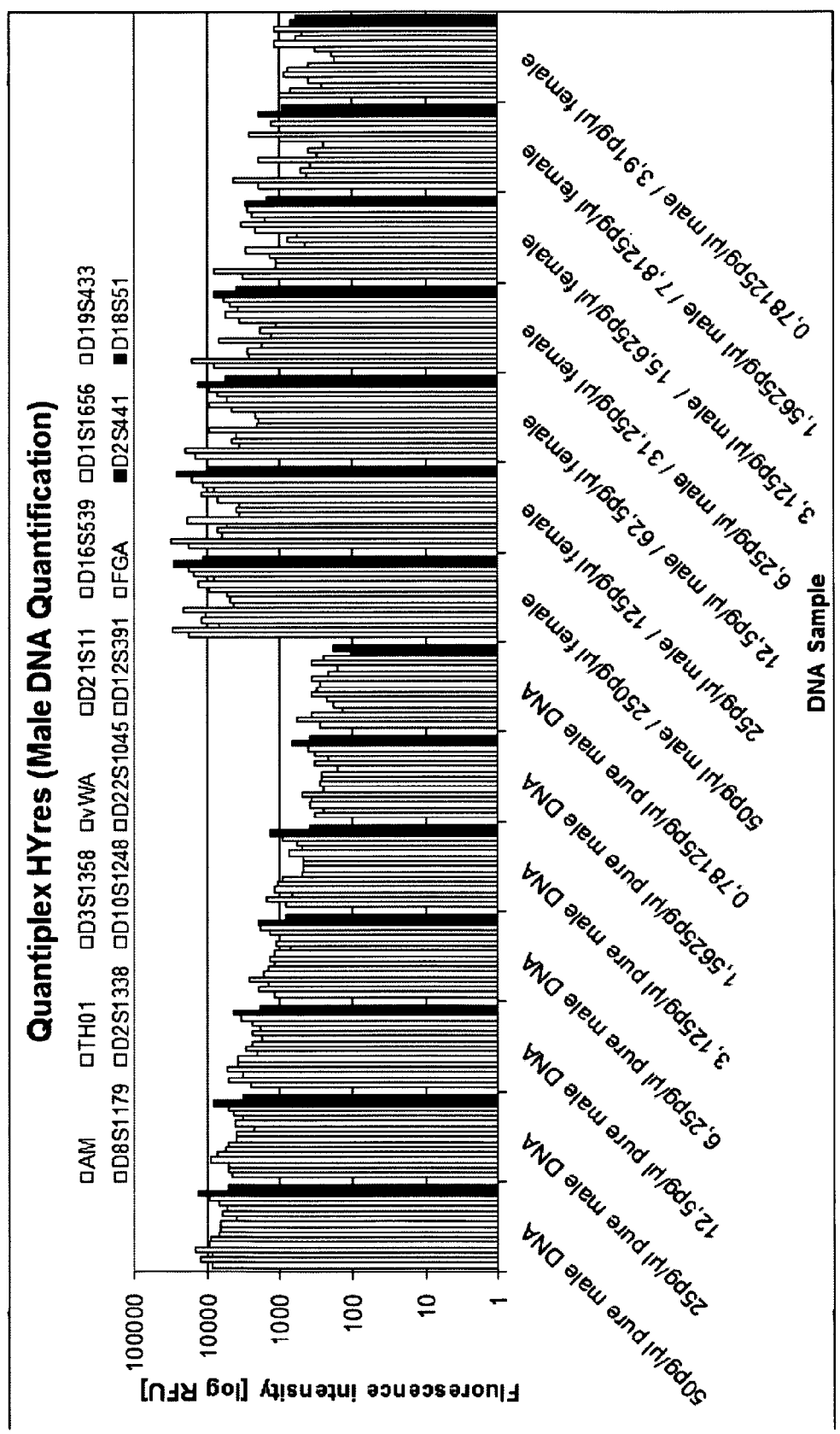

FIG. 13 shows the importance of high sensitivity and correct quantification (shown in FIG. 12) by means of STR analysis following the quantification reaction. In FIG. 13 the serial dilution of human DNA from FIG. 12 was used to generate the shown STR profiles following the protocol for the Investigator ESSplex Plus Kit (Qiagen). It demonstrates the possibility to obtain a complete STR profile even from the lowest concentration used in FIG. 12, demonstrating the usefulness of highly accurate quantification even of low template amounts.

FIG. 14

Figure 14:
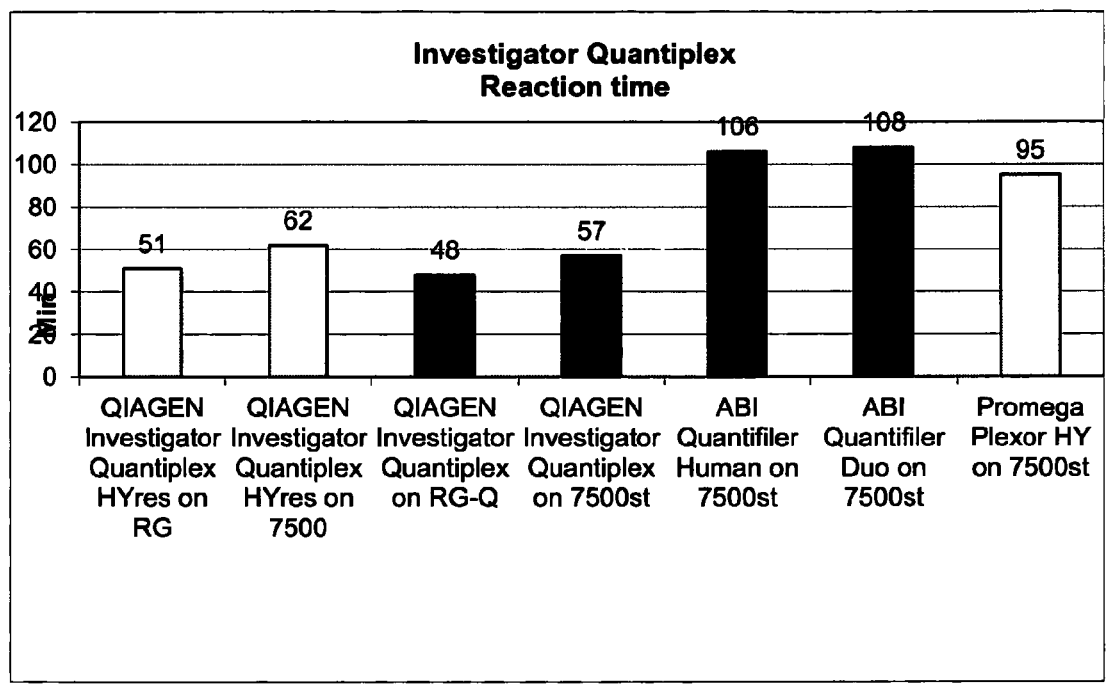

FIG. 14 further demonstrates the advantages of the invention by minimized reaction time. The "QIAGEN Investigator Quantiplex HYres" stands for a special embodiment of the method in scope of the invention. The first column (from left) shows the run time of the QIAGEN Investigator Quantiplex HYres" method on the Rotor-Gene Q real-time PCR instrument (QIAGEN). Column 2 show the run time of the "QIAGEN Investigator Quantiplex HYres" method on the 7500 PCR System from Applied Biosystems. For comparison, column 3 shows the run time for the QIAGEN Investigator Quantiplex Kit form QIAGEN run on the Rotor-Gene Q real-time PCR instrument (QIAGEN), column 4 shows the run time for the QIAGEN Investigator Quantiplex Kit form QIAGEN run on the 7500 Real-time PCR System from Applied Biosystems, column 5 shows the run time for Quantifier Human Kit from Applied Biosystems, run on the 7500 Real-time PCR System from Applied Biosystems, column 6 shows the run time for the Quantifier Duo Kit from Applied Biosystems run on the 7500 Real-time PCR System from Applied Biosystems, and column 7 shows the run time for the Plexor HY Kit from Promega, run on the 7500 Real-time PCR System from Applied Biosystems.

FIG. 15

Figure 15:
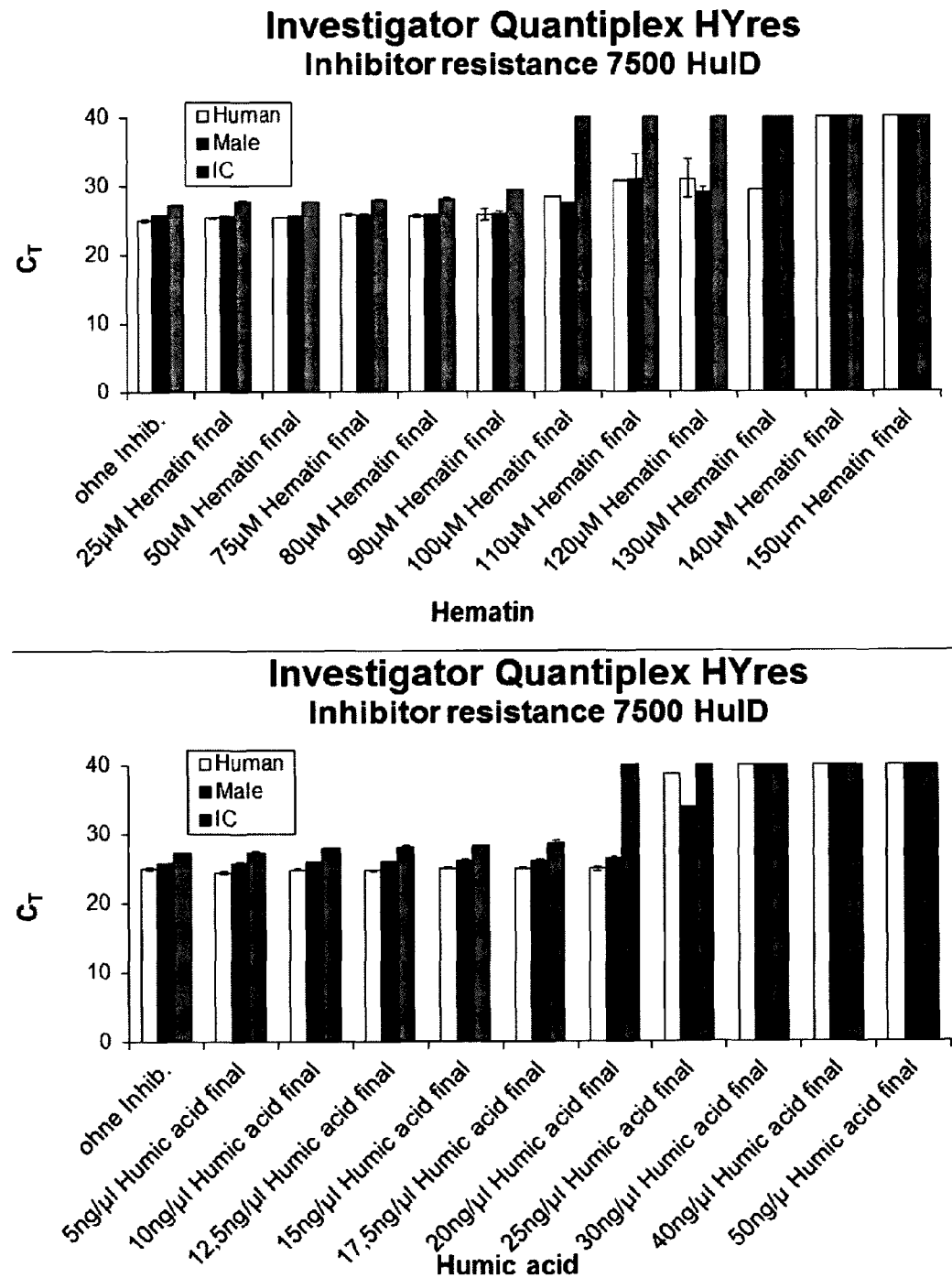

FIG. 15 shows a result using the method of the invention. The method was applied in the presence of given concentrations of the PCR inhibitors Humic Acid and Hematin.

Using the invention a high stability of the internal control to higher concentrations of inhibitors and a higher stability of the human specific target could be achieved. This gives accurate quantification even if the internal control is completely inhibited. The inhibition of the human specific target starts at a concentration between 90 and 110 µM hematin, which perfectly fits the inhibitor resistance of the Next generation STR-Kits like AmpF1STR NGM from Applied Biosystems or Investigator ESSplex from QIAGEN.

FIG. 16

FIG. 16 shows Y-MC sequences, i.e. Y chromosome multi-copy sequences. SEQ ID NO:15 serves as a reference sequence only. SEQ ID NOs:15 to 35 may also be used. As outlined above, the method may also use only the Y chromosome sequences.

EXAMPLES

The quantification of human DNA is an essential step for the set-up of STR reactions in the forensic field. Many different kits are currently available on the market for quantifying DNA (Quantifiler Human, Quantifiler Y, Quantifier Duo, Plexor HY), but all these kits have different disadvantages, such as the PCR product which is amplified on the human DNA is short and not representative for degraded DNA, the reaction is time-consuming, the chosen target is not stable in different populations or individuals.

The PCR product of the first nucleic acid is 146 bp. A reaction time of 48 minutes was achieved. This is in parts due to the fast PCR reaction chemistry with a pH range between 8 and 9 and containing $NH_4^+$, $K^+$ and $Mg^{2+}$ ions and the presence of a fast hot start enzyme with a non-chemical hot-start method such as antibody, aptamer or affibodies, but also in particular to a stable multi-copy target providing higher sensitivity and reliability combined with an internal control which reports the presence of inhibitors, but still gives a good quantification result. This internal control has a stable Ct value over the whole DNA concentration range.

The first and most surprising result is the high reaction speed due to the components of this invention. The combination of a fast non-chemical hot-start DNA polymerase, such as due to an antibody, aptamer or affibodies, a reaction buffer containing $NH^{4+}$, $K^+$ and $Mg^{2+}$ ions, and the use of preferably also scorpion primers for detecting the multi-copy lead to this result. The reactions were carried out in a reaction buffer containing Tris-HCl, pH between 8.0 and 8.8, potassium salt, preferably chloride or sulfate, ammonium salt, preferably chloride or sulfate, magnesium chloride, each dNTP, 2.5 U of the indicated heat-stable DNA polymerase and 0.1 µM of each of the forward and reverse primers given in Table 1.

TABLE 1

| | | | Sequences |
|---|---|---|---|
| Human target | 4N-S1C Pr | SEQ ID NO: 12 | 5'-CCGGGAAGCAGAAGGTGG-3' |
| | 4N-S1C | SEQ ID NO: 11 | 5'-Fam-CGAGCTCAGTTGTGCCTGTAGAGCTCG-dabcyl-C18-ACCTCTTCCTCTTGGCTGGG-3' |

TABLE 1-continued

| | | | Sequences |
|---|---|---|---|
| IC | AT-IC Rev | SEQ ID NO: 13 | 5'-GCTATCCAGTGTGCCTAGGCAA-3' |
| | AT-IC_Yak | SEQ ID NO: 14 | 5'-YAK-TGGCGTAGTCGTTCAACGCCA Dabcyl HEG CCACGAGCGTACTTCGA CTGAA-3' |

The reaction chemistry also contained commercially available PEG-8000, a polyethylene glycol having a molecular weight of about 8000 Dalton. The reaction also contained Bovine Serum Albumine (BSA).

Other methods in the state of the art are much more time-consuming. One the other side, this combination allows for more sensitive and more reliable detection of the multi-copy target and hence a better quantification of the amount of DNA. The primers in Table 1 amplify a non-repetitive multi-copy target on the genome. The great advantage in using a multi-copy target is the high sensitivity, which can be achieved. The stability of this target region within different populations was also now shown in a multi-center study, where the copy number was measured for individuals belonging to different ethnic groups (see figure below).

It is important in the forensic field to have a quantification tool, which is very sensitive, and on the other hand, which shows a real negative signal in cases where no DNA is contained in the sample. After quantification using the Quantifier Human, no reliable quantification was possible under a concentration of 6.25 pg/µl. In this case, the user would not try to obtain the STR profile and classify the sample as "non-containing DNA" (FIG. 2 below). Using the Plexor HY Kit there was little difference in the signal between low concentration samples and the NTCs.

Using the present invention the quantification in such a DNA concentration range is possible and even a full STR-profile can be obtained (FIG. 3). This result shows that this reliable quantification has a better correlation to the expected result of the STR-profile. In fact, it helps not to miss any STR-profile using very low amounts of DNA and avoids analyzing a sample which definitely does not contain DNA.

The ideal internal control in DNA quantification for forensic applications is a PCR system which should indicate the presence of PCR inhibitors in the sample without compromising the quantification of the DNA. The quantification result should be as stable as possible, also in the presence of PCR inhibitors, in order to give the user the possibility to further make use of the quantification data for the DNA fingerprinting reaction set-up.

Using Identifiler the DNA fingerprinting reaction works until a hematin concentration of 20 µM is reached.

The so-called "next generation STR-Kits" are much more resistant to the presence of inhibitors, in the example below up to 75 µM hematin may be added.

The typical forensic workflow suggests the quantification of the DNA before the STR reaction is carried out. This is done to determine how much DNA was obtained from a sample, e.g. collected from a crime scene, and how much of this DNA should be used in an STR reaction. The typical STR reaction works optimally in a certain range of template DNA and the analysis is very labor-intensive, therefore methodologies are needed that ensure a very high success rate. Therefore, it is a real advantage that the present invention enables the user not only to surely quantify the amount of DNA present but also to assess the absence of inhibitors, which could compromise the STR-reaction result, which would result in failure or loss of valuable sample material.

Some examples of inhibitor sensitivity in quantification reactions are shown in the plots below.

Plexor HY may be found here: www.promega.com/plexorhy/an157.pdf.

Quantifier Human may be found here: www3.appliedbiosystems.com/cms/groups/applied_markets_suppor-t/documents/general documents/cms_pdf.

Quantifier Duo may be found here: www.appliedbiosystems.com.br/site/material/5q7aqqbm.pdf.

Only the combined Quantifier Human and Y kits show a slightly lower stability of the internal control target in comparison to the human target. In this case, the Ct value of the IC shifts to higher values when an inhibitor is contained in the DNA sample, while the Ct value of the Human and the Y kits remain stable, at least for smaller amounts of hematin. In the case of the Quantifier human and Y Kits the resistance to inhibitors such as hematin is quite little (between 16 μM and 20 μM hematin in the reaction).

The internal control system in the Quantifier Duo Kit is more stable than the human specific target in the presence of inhibitors. The utility of the internal control system in this case is of course low because the internal control system does not give any indication of the presence of inhibitors in the sample while the DNA quantification is already compromised. In fact, the Ct values of the RPPH1 and of the SRY systems shift to higher values even at low amounts of inhibitors. The dramatic increase of the Ct value of the RPPH1 system to >40 in the presence of 12.5 μM hematin makes the quantification of the human DNA impossible.

The resistance to the presence of inhibitors in the sample is very low in comparison to the new generation STR-kits (i.e. 10 μM hematin and 3.75 ng/μl humic acid).

The Plexor HY Kit shows quite the same stability of the internal control target in comparison to the human target. In this case, the Ct value of the IC shifts to higher values when an inhibitor is contained in the DNA sample. Even the Ct value of the human specific target shifts to higher levels when the inhibitor is contained in the sample, thus making correct DNA quantification difficult. In the case of the Plexor HY the resistance to inhibitors such as hematin is quite little (ca. 25 μM hematin in the reaction).

We could achieve a high stability of the internal control to high concentrations of inhibitors and a higher stability of the human specific target, which gives accurate quantification even if the internal control is completely inhibited. The inhibition of the human specific target starts at a concentration between 80 and 100 μM hematin, which perfectly fits the inhibitor resistance of the Next generation STR-Kits (such as the ABI NGM™ kit).

It is known that real-time PCR is based on the real-time detection of the amplification of a PCR product. Actually, the length of this PCR product for DNA quantification purposes in forensic is very important. In fact, the quantification of DNA is the first step towards a DNA fingerprinting analysis, which is typically the analysis of short tandem repeats (STR). These repeats are analyzed in a multiplex-reaction where different loci are amplified through PCR in the same reaction well. The amplification product of these loci can vary from about 100 bp up to about 450 bp, depending on the loci, that have to be analyzed.

In the case of degraded DNA, which can occur for example when a stain has been exposed to stress factors such as light, the mean fragment length of the human DNA is reduced and often the longest loci are not amplifiable anymore. If the quantification assay detects shorter DNA fragments, it may overestimate the quantity of STR-sized fragments, resulting in a relatively high proportion of under-amplified and undetected STR alleles, which is an undesirable result. Therefore, we choose a longer fragment to be amplified for quantification purposes.

The invention claimed is:

1. A method of quantifying and/or detecting one or more nucleic acids of a genome in a sample, the method comprising:
   a. amplifying, in a reaction well or a reaction vial, a nucleic acid comprising a non-repetitive, multicopy locus, within the genome, the multicopy locus having copies on at least 2 chromosomes and a sequence that shares at least 80% sequence identity over a stretch of 80 base pairs to a nucleic acid sequence of SEQ ID NO:1 to produce a first amplification product;
   b. amplifying, in parallel in the reaction well or the reaction vial, an internal control nucleic acid sequence to produce a second amplification product;
   c. detecting the first and the second amplification products; and
   d. quantifying the first and the second amplification products;
   wherein amplifying the internal control nucleic acid sequence comprises amplifying with at least one primer sequence selected from the group consisting of SEQ ID NO:13 and SEQ ID NO:14.

2. The method according to claim 1, further comprising:
   a. amplifying, in parallel in the reaction well or the reaction vial, a nucleic acid comprising a non-repetitive, multicopy locus, on the Y-chromosome within the genome, the locus having a sequence that shares at least 80% sequence identity over a stretch of 80 base pairs to a nucleic acid sequence of SEQ ID NO:15 to produce a third amplification product;
   b. detecting the first, the second and the third amplification products; and
   c. quantifying the first, the second and the third amplification products.

3. The method according to claim 2, wherein amplifying the nucleic acid comprising the non-repetitive, multicopy locus, on the Y-chromosome within the genome comprises amplifying with primers that have a nucleotide sequence that differs from SEQ ID NO: 2, 3, 5, 6, 8, 9, 10, 11 and/or 12 by no more than 5 nucleotides over a stretch of 18 nucleotides.

4. The method according to claim 2, wherein the third amplification product is between 60 base pairs and 200 base pairs long.

5. The method according to claim 2, wherein the quantity of the amplification products is determined either during the amplifying of nucleic acids or at the end of the amplifying of nucleic acids.

6. The method according to claim 1, wherein the first amplification product is between 60 base pairs and 200 base pairs long.

7. The method according to claim 1, wherein the second amplification product is between 60 base pairs and 400 base pairs long.

8. The method according to claim 1, wherein the second amplification product is between 100 base pairs and 400 base pairs long.

9. The method according to claim 1, wherein the second amplification product is longer than the first amplification product.

10. The method according to claim 1, comprising between 100 to 5000 copies of the internal control nucleic acid sequence.

11. The method according to claim 1, wherein the quantity of the amplification products is determined either during the amplifying of nucleic acids or at the end of the amplifying of nucleic acids.

12. The method according to claim 1, wherein the reaction well or the reaction vial comprises one or more of:
   a) Tris-HCl at a pH of between 8 and 8.8;
   b) potassium salt selected from the group consisting of potassium chloride and potassium sulphate;
   c) an ammonium salt selected from the group consisting of ammonium chloride and ammonium sulphate;
   d) magnesium chloride; and
   e) a hot-start polymerase.

13. A method of quantifying and/or detecting one or more nucleic acids of a genome in a sample, the method comprising:
   a. amplifying, in a reaction well or a reaction vial, a nucleic acid comprising a non-repetitive, multicopy locus, on the Y-chromosome within the genome, the locus having a sequence that shares at least 80% sequence identity over a stretch of 80 base pairs to a nucleic acid sequence of SEQ ID NO:15 to produce a first amplification product;
   b. amplifying, in parallel in the same reaction well or vial, an internal control nucleic acid sequence to produce a second amplification product;
   c. detecting the first and the second amplification products; and
   d. quantifying the first and the second amplification products;
   wherein amplifying the internal control nucleic acid sequence comprises amplifying with at least one primer sequence selected from the group consisting of SEQ ID NO:13 and SEQ ID NO:14.

14. The method according to claim 13, wherein amplifying the nucleic acid comprising the non-repetitive, multicopy locus, on the Y-chromosome within the genome comprises amplifying with primers that have a nucleotide sequence that differ from SEQ ID NO: 2, 3, 5, 6, 8, 9, 10, 11 and/or 12 by no more than 5 nucleotides over a stretch of 18 nucleotides.

15. The method according to claim 13, wherein the first amplification product is between 60 base pairs and 200 base pairs long.

16. The method according to claim 13, wherein the second amplification product is between 60 base pairs and 400 base pairs long.

17. The method according to claim 13, wherein the second amplification product is between 100 base pairs and 400 base pairs long.

18. The method according to claim 13, wherein the second amplification product is longer than the first amplification product.

19. The method according to claim 13, comprising between 100 to 5000 copies of the internal control nucleic acid.

20. The method according to claim 13, wherein the reaction well or the reaction vial comprises one or more of:
   a) Tris-HCl at a pH of between 8 and 8.8;
   b) potassium salt selected from the group consisting of potassium chloride and potassium sulphate;
   c) an ammonium salt selected from the group consisting of ammonium chloride and ammonium sulphate;
   d) magnesium chloride; and
   e) a hot-start polymerase.

21. The method according to claim 13, wherein the quantity of the amplification products is determined either during the amplifying of nucleic acids or at the end of the amplifying of nucleic acids.

* * * * *